(12) United States Patent
Linstedt et al.

(10) Patent No.: US 11,730,730 B2
(45) Date of Patent: Aug. 22, 2023

(54) CELL-BASED SCREENING AND COMPOUNDS THAT MODULATE GALNAC-TRANSFERASES

(71) Applicant: Carnegie Mellon University, Pittsburgh, PA (US)

(72) Inventors: Adam D. Linstedt, Pittsburgh, PA (US); Lina Song, Gainesville, FL (US); Collin Bachert, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 106 days.

(21) Appl. No.: 17/330,779

(22) Filed: May 26, 2021

(65) Prior Publication Data

US 2021/0283124 A1    Sep. 16, 2021

Related U.S. Application Data

(62) Division of application No. 16/369,159, filed on Mar. 29, 2019, now Pat. No. 11,058,675.

(60) Provisional application No. 62/761,585, filed on Mar. 29, 2018.

(51) Int. Cl.
| | |
|---|---|
| *A61K 31/4709* | (2006.01) |
| *A61P 13/12* | (2006.01) |
| *A61P 35/04* | (2006.01) |
| *G01N 33/50* | (2006.01) |
| *G01N 33/533* | (2006.01) |
| *C12Q 1/48* | (2006.01) |

(52) U.S. Cl.
CPC .......... *A61K 31/4709* (2013.01); *A61P 13/12* (2018.01); *A61P 35/04* (2018.01); *G01N 33/5008* (2013.01); *G01N 33/533* (2013.01)

(58) Field of Classification Search
None
See application file for complete search history.

(56) References Cited

U.S. PATENT DOCUMENTS

| | | |
|---|---|---|
| 2005/0249718 A1 | 11/2005 | Sprecher et al. |
| 2011/0159519 A1 | 6/2011 | Schmidt et al. |
| 2012/0058494 A1 | 3/2012 | Bruchez et al. |
| 2013/0244891 A1 | 9/2013 | Waggoner et al. |

FOREIGN PATENT DOCUMENTS

| | | |
|---|---|---|
| WO | 0185215 A2 | 11/2001 |
| WO | 2008046085 A2 | 4/2008 |

OTHER PUBLICATIONS

Bachert et al., "A Sensor of Protein O-Glycosylation Based on Sequential Processing in the Golgi apparatus", Traffic, Jan. 2013, pp. 47-56, vol. 14:1.

Bai et al., "CYP24 inhibition as a therapeutic target in FGF23-mediated renal phosphate wasting disorders", The Journal of Clinical Investigation, 2016, pp. 667-680, vol. 126:2.

Bennett et al., "Control of mucin-type O-glycosylation: A classification of the polypeptide GalNAc-transferase gene family", Glycobiology, 2012, pp. 736-756, vol. 22:6.

Brockhausen, "Mucin-type O-glycans in human colon and breast cancer: glycodynamics and functions", European Molecular Biology Organization Reports, 2006, pp. 599-604, vol. 7:6.

Brooks et al., "Immunolocalisation of members of the polypeptide N-acetylgalactosaminyl transferase (ppGalNAc-T) family is consistent with biologically relevant altered cell surface glycosylation in breast cancer", Acta Histochemica, 2007, pp. 273-284, vol. 109.

Chefetz et al., "Familial tumoral calcinosis and the role of O-glycosylation in the maintenance of phosphate homeostasis", Biochimica et Biophysica Acta, 2009, pp. 847-852, vol. 1792.

Cranfill et al., "Quantitative Assessment of Fluorescent Proteins", Nat Methods, Jul. 2016, pp. 557-562, vol. 13:7.

Degirolamo et al., "Therapeutic potential of the endocrine fibroblast growth factors FGF19, FGF21 and FGF23", Nature Reviews, Jan. 2016, pp. 51-69, vol. 15.

Eckardt et al., "Kidney Disease: Improving Global Outcomes", Nat. Rev. Nephrol, 2009, pp. 650-657, vol. 5.

Evan et al., "Isolation of Monoclonal Antibodies Specific for Human c-myc Proto-Oncogene Product", Molecular and Cellular Biology, Dec. 1985, pp. 3610-3616, vol. 5:12.

Falco et al., "scFv-based fluorogen activating proteins and variable domain inhibitors as fluorescent biosensor platforms", Biotechnology Journal, Sep. 2009, pp. 1328-1336, vol. 4.

Fukumoto, "FGF23-FGF Receptor/Klotho Pathway as a New Drug Target for Disorders of Bone and Mineral Metabolism", Calcif Tissue Int, 2016, pp. 334-340, vol. 98.

Gao et al., "Expression pattern of polypeptide N-acetylgalactosaminyltransferase-10 in gastric carcinoma", Oncology Letters, 2013, pp. 113-116, vol. 5.

Goetz et al., "Isolated C-terminal tail of FGF23 alleviates hypophosphatemia by inhibiting FGF23-FGFR-Klotho complex formation", PNAS, Jan. 5, 2010, pp. 407-412, vol. 107:1.

Harada et al., "Strong expression of polypeptide N-acetylgalactosaminyltransferase 3 independently predicts shortened disease-free survival in patients with early stage oral squamous cell carcinoma", Tumor Biol., 2016, pp. 1357-1368, vol. 37.

Ichikawa et al., "Genetic Rescue of Glycosylation-deficient Fgf23 in the Galnt3 Knockout Mouse", Endocrinology, Oct. 2014, pp. 3891-3898, vol. 155:10.

Isakova et al., "Rationale and Approaches to Phosphate and Fibroblast Growth Factor 23 Reduction in CKD", Journal of the American Society of Nephrology, 2015, pp. 2328-2339, vol. 26.

Jesch et al., "Mitotic Phosphorylation of Golgi Reassembly Stacking Protein 55 by Mitogen-activated Protein Kinase ERK2", Molecular Biology of the Cell, Jun. 2001, pp. 1811-1817, vol. 12.

(Continued)

*Primary Examiner* — Suzanne M Noakes
*Assistant Examiner* — Jae W Lee
(74) *Attorney, Agent, or Firm* — The Webb Law Firm

(57) ABSTRACT

Provided herein are small molecule-inhibitors of site-specific O-glycosylation and the identification of such using cell-based fluorescent biosensors. Also provided herein are methods of treating kidney disease and cancer, such as breast cancer.

9 Claims, 30 Drawing Sheets

Specification includes a Sequence Listing.

(56) References Cited

OTHER PUBLICATIONS

Kato et al., "Polypeptide GalNAc-transferase T3 and Familial Tumoral Calcinosis", The Journal of Biological Chemistry, Jul. 7, 2006, pp. 18370-18377, vol. 281:27.

Kitada et al., "Polypeptide N-acetylgalactosaminyl transferase 3 independently predicts high-grade tumours and poor prognosis in patients with renal cell carcinomas", British Journal of Cancer, 2013, pp. 472-481, vol. 109.

Kohsaki et al., "Expression of UDP-GalNAc: polypeptide N-acetylgalactosaminyltransferase isozymes T1 and T2 in human colorectal cancer", Journal of Gastroenterology, 2000, pp. 840-848, vol. 35.

Kuan et al., "Inhibition of Mucin Glycosylation by Aryl-N-Acetyl-α-galactosaminides in Human Colon Cancer Cells", The Journal of Biological Chemistry, Nov. 15, 1989, pp. 19271-19277, vol. 264:32.

Lambert, "FPbase: a community-editable fluorescent protein database", Nature Methods, Apr. 2019, pp. 277-280, vol. 16.

Mochizuki et al., "Expression of Polypeptide N-Acetylgalactosaminyl Transferase-3 and Its Association with Clinicopathological Factors in Thyroid Carcinomas", Thyroid, 2013, pp. 1553-1560, vol. 23:12.

Moremen et al., "Vertebrate protein glycosylation: diversity, synthesis and function", Nature Reviews, Jul. 2012, pp. 448-462, vol. 13.

Mukhopadhyay et al., "Manganese-induced Trafficking and Turnover of the cis-Golgi Glycoprotein GPP130", Molecular Biology of the Cell, Apr. 1, 2010, pp. 1282-1292, vol. 21.

Patsos et al., "O-Glycan inhibitors generate aryl-glycans, induce apoptosis and lead to growth inhibition in colorectal cancer cell lines", Glycobiology, 2009, pp. 382-398, vol. 19:4.

Peng et al., "MicroRNA-214 Suppresses Growth and Invasiveness of Cervical Cancer Cells by Targeting UDP-N-acetyl-α-D-galactosamine:Polypeptide N-Acetylgalactosaminyltransferase 7", The Journal of Biological Chemistry, Apr. 20, 2012, pp. 14301-14309, vol. 287:17.

Puri et al., "Cycling of Early Golgi Proteins Via the Cell Surface and Endosomes Upon Lumenal pH Disruption", Traffic, 2002, pp. 641-653, vol. 3.

Revoredo et al., "Mucin-type O-glycosylation is controlled by short- and long-range glycopeptide substrate recognition that varies among members of the polytide GalNAc transferase family", Glycobiology, 2016, pp. 360-376, vol. 26:4.

Rottger et al., "Localization of three human polypeptide GalNAc-transferases in HeLa cells suggests initiation of O-linked glycosylation throughout the Golgi apparatus", Journal of Cell Science, 1998, pp. 45-60, vol. 111.

Rowe, "A unified model for bone-renal mineral and energy metabolism", Current Opinion in Pharmacology, 2015, pp. 64-71, vol. 22.

Saunders et al., "Fluorogen Activating Proteins in Flow Cytometry for the Study of Surface Molecules and Receptors", Methods, Jul. 2012, pp. 308-317, vol. 57:3.

Schjoldager et al., "O-Glycosylation Modulates Proprotein Convertase Activation of Angiopoietin-Like Protein 3", The Journal of Biological Chemistry, Nov. 19, 2010, pp. 36293-36303, vol. 285:47.

Schjoldager et al., "A Systematic Study of Site-specific GalNAc-type O-Glycosylation Modulating Proprotein Convertase Processing", The Journal of Biological Chemistry, Nov. 18, 2011,pp. 40122-40132, vol. 286:46.

Schjoldager et al., "Probing isoform-specific functions of polypeptide GalNAc-transferases using zinc finger nuclease glycoengineered SimplecCells", PNAS, Jun. 19, 2012, pp. 9893-9898, vol. 109:25.

Schjoldager et al., "Site-specific protein O-glycosylation modulates proprotein processing—Deciphering specific functions of the large polypeptide GalNAc-transferase gene family", Biochimica et Biophysica Acta, 2012, pp. 2079-2094, vol. 1820.

Schjoldager et al., "Deconstruction of O-glycosylation—GalNAc-T isoforms direct distinct subsets of the O-glycoproteome", EMBO Reports, 2015, pp. 1713-1722, vol. 16.

Simon et al., "Site-specific glycosylation of Ebola virus glycoprotein by human polypeptide GalNAc-transferase 1 induces cell adhesion defects", J. Biol. Chem, Nov. 2, 2018, pp. 1-15.

Smith, "The Use of Fibroblast Growth Factor 23 Testing in Patients with Kidney Disease", Clinical Journal of the American Society of Nephrology, Jul. 2014, pp. 1283-1303, vol. 9.

Song et al., "Development of Isoform-specific Sensors of Polypeptide GalNAc-transferase Activity", The Journal of biological Chemistry, Oct. 31, 2014, pp. 30556-30566, vol. 289:44.

Sun et al., "FGF23 neutralization improves bone quality and osseointegration of titanium implants in chronic kidney disease mice", Scientific Reports, Feb. 10, 2015, pp. 1-7.

Szasz et al., "Cross-validation of survival associated biomarkers in gastric cancer using transcriptomic data of 1,065 patients", Oncotarget, Jun. 30, 2016, pp. 49322-49333, vol. 7:31.

Szent-Gyorgyi et al., "Fluorogen-activating single-chain antibodies for imaging cell surface proteins", Nature Biotechnology, Feb. 2008, pp. 235-240, vol. 26:2.

Tagliabracci et al., "Dynamic regulation of FGF23 by Fam20C phosphorylation, GalNAc-T3 gylcosylation, and furin proteolysis", PNAS, Apr. 15, 2014, pp. 5520-5525, vol. 111:15.

Van Der Post et al., "Site-specific O-Glycosylation on the MUC2 Mucin Protein Inhibits Cleavage by the Porphyromonas gingivalis Secreted Cysteine Protease (RgpB)", The Journal of Biological Chemistry, May 17, 2013, pp. 14636-14646, vol. 288:20.

Wang et al., "Role of the polypeptide N-acetylgalactosaminyltransferase 3 in ovarian cancer progression: possible implications in abnormal mucin O-glycosylation", Oncotarget, Jan. 27, 2014, vol. 5:2.

```
SEQ ID NO: 1:
ATGGAGACAGACACACTCCTGCTATGGGTACTGCTGCTCTGGGTTCCAGGTTCCACTGGTGACTA
TCCATATGATGTGCCAGATTATGCTGGGGCCCAGCCGGCCTACCCATACGACGTTCCAGACTACG
CTCTGCAGGCTAGTGGTGGTGGTGGTTCTGGTGGTGGTGGTTCTGCTAGCCAGGTGCAGCTGGTG
GAGTCTGAGGGAGGCTTGGTACAGCCTGGAGGGTCCCTGAGACTCTCCTGTGCAGCCTCTGGATT
CACCTTCAGTAGTTATGAAATGAACTGGGTCCGCCAGGCTCCAGGTAAGGGGCTGGAGTGGGTCT
CACGTATTGATGGTGATGGGAGCAGCACAAACTACGCGGACTCCGTGAAGGGCCGATTCACCATC
TCCAGAGACAACGCCAAGAGCACGCTGTATCTGCAAATGAATAGTCTGAGAGCCGAGGACACGGC
TGTGTATTACTGTACAAGGGCCAGATACTTTGGTTCGGTGAGCCCCTACGGTATGGACGTCTGGG
GCCAAGGGACCACGGTCACCGTCTCCTCAGGAATTCTAGGATCGAACTCGAGAGAGGACAGAGTC
ACCGGTAGCTACCAGGGTGGCGGTGGCAGCGGCGGTGGTGGTTCCGGAGGCGGCGGTTCTCAGGC
TGTGGTGACTCAGGAGCCGTCAGTGACTGTGTCCCCAGGAGGGACAGTCATTCTCACTTGTGGCT
CCAGCACTGGAGCTGTCACCAGCGGTCATTATGCCAACTGGTTCCAGCAGAAGCCTGGCCAAGCC
CCCAGGGCACTTATATTTGAAACCGACAAGAAATATTCCTGGACCCCTGGCCGATTCTCAGGCTC
CCTCCTTGGGGCCAAGGCTGCCCTGACCATCTCGGATGCGCAGCCTGAAGATGAGGCTGAGTATT
ACTGTTCGCTCTCCGACGTAGACGGTTATCTGTTCGGAGGAGGCACCCAGCTGACCGTCCTATCC
GGAATTGGCCGCAGGGGCCGGGATCCGCGGCTGCAGGTCGACGAACAAAAACTCATCTCAGAAGA
GGATCTGAATGCTGTGGGCCAGGACACGCAGGAGGTCATCGTGGTGCCACACTCCTTGCCCTTTA
AGGTGGTGGTGATCTCAGCCATCCTGGCCCTGGTGGTGCTCACCATCATCTCCCTTATCATCCTC
ATCATGCTTTGGCAGAAGAAGCCACGTCCACAGCCGGCCAGCAAGGGCGAGGAGCTGTTCACCGG
GGTGGTGCCCATCCTGGTCGAGCTGGACGGCGACGTAAACGGCCACAAGTTCAGCGTGTCCGGCG
AGGGCGAGGGCGATGCCACCTACGGCAAGCTGACCCTGAAGCTGATCTGCACCACCGGCAAGCTG
CCCGTGCCCTGGCCCACCCTCGTGACCACCCTGGGCTACGGCCTGCAGTGCTTCGCCCGCTACCC
CGACCACATGAAGCAGCACGACTTCTTCAAGTCCGCCATGCCCGAAGGCTACGTCCAGGAGCGCA
CCATCTTCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGGGCACAA
GCTGGAGTACAACTACAACAGCCACAACGTCTATATCACCGCCGACAAGCAGAAGAACGGCATCA
AGGCCAACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTACCAGTC
CGCCCTGAGCAAAGACCCCAACGAGAAGCGCGATCACATGGTCCTGCTGGAGTTCGTGACCGCCG
CCGGGATCACTCTCGGCATGGACGAGCTGTACAAGTAA

SEQ ID NO: 2:
GLY:    REDRVTGSYQG
SEQ ID NO. 3:
ΔGLY:   REDRVAGSYQG

SEQ ID NO: 4:
METDTLLLWVLLLWVPGSTGDYPYDVPDYAGAQPAYPYDVPDYALQASGGGGSGGGGSAS
QVQLVESEGGLVQPGGSLRLSCAASGFTFSSYEMNWVRQAPGKGLEWVSRIDGDGSSTNY
ADSVKGRFTISRDNAKSTLYLQMNSLRAEDTAVYYCTRARYFGSVSPYGMDVWGQGTTVT
VSSGILGSNSREDRVTGSYQGGGGSGGGGSGGGGSQAVVTQEPSVTVSPGGTVILTCGSS
TGAVTSGHYANWFQQKPGQAPRALIFETDKKYSWTPGRFSGSLLGAKAALTISDAQPEDE
AEYYCSLSDVDGYLFGGGTQLTVLSGIGRRGRDPRLQVDEQKLISEEDLNAVGQDTQEVI
VVPHSLPFKVVVISAILALVVLTIISLIILIMLWQKKPRPQPASKGEELFTGVVPILVEL
DGDVNGHKFSVSGEGEGDATYGKLTLKLICTTGKLPVPWPTLVTTLGYGLQCFARYPDHM
KQHDFFKSAMPEGYVQERTIFFKDDGNYKTRAEVKFEGDTLVNRIELKGIDFKEDGNILG
HKLEYNYNSHNVYITADKQKNGIKANFKIRHNIEDGGVQLADHYQQNTPIGDGPVLLPDN
HYLSYQSALSKDPNEKRDHMVLLEFVTAAGITLGMDELYK*
```

*FIG. 10*

L5-MG (SEQ ID NO: 5)

QAVVTQEPSVTVSPGGTVILTCGSSTGAVTSGHYANWFQQKPGQAPR
ALIFETDKKYPWTPGRFSGSLLGVKAALTISDAQPEDEAEYYCLLSDVDGYL
FGGGTQLTVLS

L5-MG E52D (SEQ ID NO: 6)

QAVVTQEPSVTVSPGGTVILTCGSSTGAVTSGHYANWFQQKPGQAPR
ALIFDTDKKYPWTPGRFSGSLLGVKAALTISDAQPEDEAEYYCLLSDVDGYL
FGGGTQLTVLS

L5-MG L91S (SEQ ID NO: 7)

QAVVTQEPSVTVSPGGTVILTCGSSTGAVTSGHYANWFQQKPGQAPR
ALIFETDKKYPWTPGRFSGSLLGVKAALTISDAQPEDEAEYYCSLSDVDGYL
FGGGTQLTVLS

L5-MG E52D L91S (SEQ ID NO: 8)

QAVVTQEPSVTVSPGGTVILTCGSGTGAVTSGHYANWFQQKPGQAPR
ALIFDTDKKYPWTPGRFSGSLLGVKAALTISDAQPEDEAEYYCSLSDVDGYL
FGGGTQLTVLS

*Figure 11A*

**HL4-MG core 251aa *(SEQ ID NO: 9)***

QVQLVESEGGLVQPGGSLRLSCAASGFTFSSYEMNWVRQAPGKGLEWVSRIDGD
GSSTNYADSVKGRFTISRDNAKSTLYLQMNSLRAEDTAVYYCTRARYFGSVSPYGM
DVWGQGTTVTVSSGILGSGGGGSGGGGSGGGGSDIRVTQSPSSVSASVGDRVTISC
RASQGIATWLGWYQQKPGKPPQLLIYSASTLQTGVPSRFSGSGSGTDFTLTISSLQP
EDVATYYCQEGSTFPLTFGGGTKVDIKS

**H6-MG in PNL6 core 130aa *(SEQ ID NO: 10)***

QVQLQESGPGLVKPSETLSLTCTVSGASISSSHYYWGWIRQPPGKGPEWIGSMYYS
GRTYYNPALKSRVTISPDKSKNQFFLKLTSVTAADTAVYYCAREGPTHYYDNSGPIP
SDEYFQHWGQGTLVTVS

**L9-MG secreted form (MG67) (6aa - 114aa) 109aa *(SEQ ID NO: 11)***

SYELTQPPSVSVSPGQTARITCSGDALPKQYTYWYQQKAGQAPVLVIYKDTERPSGI
PERFSGTSSGTTVTLTISGVQAEDEADYYCQSADSSGSYVFFGGGTKVTVLS

*Figure 11B*

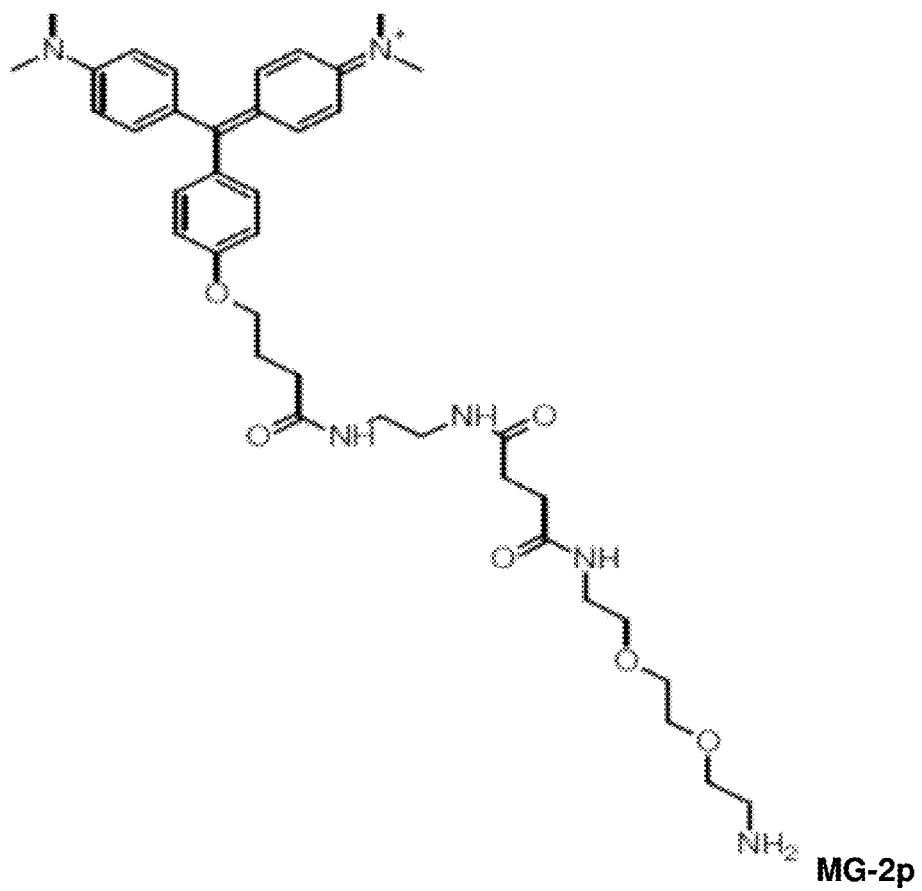
MG-2p
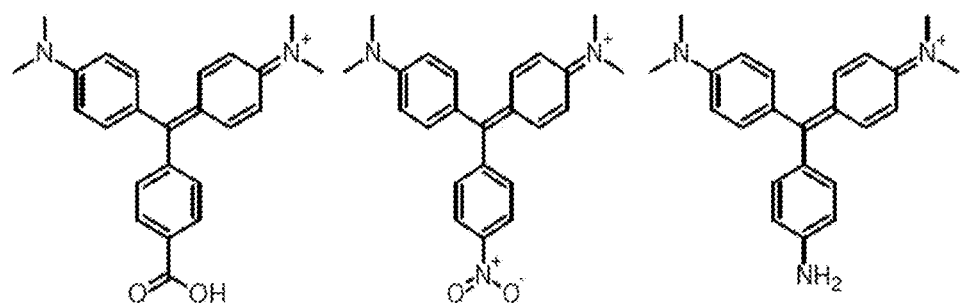
FIG. 12B

MG-11p
C₅₇H₉₁N₆O₁₆
1116.36

CELL-BASED SCREENING AND COMPOUNDS THAT MODULATE GALNAC-TRANSFERASES

CROSS REFERENCE TO RELATED APPLICATIONS

This application is a divisional application of U.S. patent application Ser. No. 16/369,159, filed Mar. 29, 2019, which claims the benefit of U.S. Provisional Patent Application No. 62/761,585, filed Mar. 29, 2018, the contents of which are incorporated herein by reference in their entirety.

STATEMENT REGARDING FEDERALLY SPONSORED RESEARCH

This invention was made with government support under Grant Nos. DE026714 and GM095549 awarded by the National Institutes of Health. The government has certain rights in this invention.

The Sequence Listing associated with this application is filed in electronic format via EFS-Web and is hereby incorporated by reference into the specification in its entirety. The name of the text file containing the Sequence Listing is 6526-1901419 ST25.txt. The size of the text file is 18,683 bytes, and the text file was created on Mar. 16, 2023.

Protein O-glycosylation is an important post-translational modification occurring in the secretory pathway. Currently there are 25 well-defined medical syndromes linked to defects in O-glycosylation. Additionally, aberrations in glycosylation may also relate to certain forms of heart disease as well as tumor formation and metastasis. O-linked glycosylation begins in early Golgi cisternae where a family of up to 20 highly conserved polypeptide N-acetylgalactosaminyl-transferases (ppGalNTases) add N-acetylgalactosamine (GalNAc) to secretory cargo on serine or threonine residues that are typically adjacent to proline residues. The subsequent additions of sugar moieties to the initial carbohydrate group are thought to proceed in an orderly fashion as cargo moves through each successive Golgi cisterna, each containing a unique mix of glycosylation extending enzymes (see, e.g., Collin Bachert and Adam Linstedt, "A Sensor of Protein O-Glycosylation Based on Sequential Processing in the Golgi apparatus", Traffic. 2013 January; 14(1): 47-56).

The ability of an added O-glycan moiety to regulate cleavage of an adjacent proteolytic processing site in newly synthesized cargo is an intriguing and medically relevant aspect of protein O-glycosylation. Glycan addition next to a protease recognition site can sterically block access of the protease to this site, and aberrations in this interplay between glycosylation and proteolysis can lead to disease. Familial Tumoral Calcinosis is thought to arise when mutations block glycosylation of the bone growth factor FGF23 thereby allowing a proprotein convertase to access and cleave the growth factor leading to its inactivation. Similarly, hypoglycosylation of apolipoprotein (a) leads to its proteolytic digestion, creating fragments in the blood stream that compete for binding to the extracellular matrix in atherosclerotic lesions. Conversely, the glycosylation of angiopoietin-like 3 blocks its processing and activation causing altered triglyceride homeostasis. Likewise, glycosylation inhibits cleavage-mediated activation of natriuretic peptide B (BNP), which regulates sodium excretion during heart failure.

The mechanism of regulation of protease sites by glycan masking is incompletely understood. A scalable, cell-based screen for defects in this process offers great promise towards identification of the full complement of the involved cellular factors. Similarly, a screen to identify small-molecule inhibitors of O-glycosylation would potentially lead to novel therapeutic approaches given that the list of known inhibitors is small, the inhibitors are toxic and offer little specificity towards individual members of the large ppGalNTase family.

SUMMARY

In one aspect, provided herein is a method for treating chronic kidney disease in a patient. The method includes: inhibiting O-glycosylation by administering to a patient in need thereof an amount of a GalNAc transferase-3 inhibitor effective to treat chronic kidney disease in a patient.

In another aspect, provided is a method for inhibiting cancer metastasis in a patient. The method includes: inhibiting O-glycosylation by administering to a patient in need thereof an amount of a GalNAc transferase-3 inhibitor effective to reduce invasiveness of cancer thereby inhibiting cancer metastasis in a patient.

In another aspect, provided is a method for identifying a compound that inhibits GalNAc transferase-1. The method includes: a.) expressing in cells a sensor comprising a polypeptide comprising, in order, an FAP blocking domain having an FAP sequence of SEQ ID NOS: 5-11, a furin cleavage linker having the sequence REDRVTGSYQ (SEQ ID NO: 2), an FAP domain of SEQ ID NOS: 5-11, a transmembrane domain, and, optionally, a fluorescent protein domain; b.) contacting the cells with a compound to be tested for GalNAc transferase 1 inhibitory activity, and an activatable malachite green fluorochrome, and c.) determining if ppGalNAc transferase-1 activity is inhibited based upon the presence or absence of fluorescence of an activatable malachite green compound that fluoresces when bound to the FAP domain of the sensor.

Also provided herein is a fluorescent sensor of GalNAc-type O-glycosylation by GalNAc-T1 isozyme including, in order, an FAP blocking domain having a sequence of an FAP of SEQ ID NOS: 5-11, a furin cleavage linker having the sequence REDRVTGSYQ (SEQ ID NO: 2), an FAP domain of any one of SEQ ID NOS: 5-11, a transmembrane domain, and, optionally, a fluorescent protein domain.

Also provided is a nucleic acid including a gene for expression of a fluorescent sensor polypeptide of GalNAc-type O-glycosylation by a GalNAc-T1, isozyme, comprising an open reading frame encoding a polypeptide comprising, in order, an FAP blocking domain having an FAP sequence of SEQ ID NOS: 5-11, a furin cleavage linker having the sequence REDRVTGSYQ (SEQ ID NO: 2), an FAP domain of SEQ ID NOS: 5-11, a transmembrane domain, and, optionally, a fluorescent protein domain.

BRIEF DESCRIPTION OF THE DRAWINGS

FIG. 1 (A) shows an example of sensor design and the linker sequences (SEQ ID NOS: 15-18) used. O-glycosylation of the linker masks the furin site but if an inhibitor blocks the ppGalNAc-transferase then furin cleaves the linker releasing the blocking domain (BD) allowing fluorescent activating protein (FAP) dimerization and dye activation. Linker furin sites are underlined and sites of glycosylation or mutation are in bold. FIG. 1 (B) provides an example of HEK cell lines with or without ppGalNAc-T2 or T3 stably expressing the WT or Δglycan T2 or T3 sensor constructs (see linkers in A) that were imaged in the presence of 110 nM of the dye MG11p (MG) to detect GFP or MG. Bar=20 μm. FIG. 1 (C) is a schematic showing cell plating, drug treatment, cell release, fluorescence measurement and parallel analysis using both T2 and T3 sensors. Hits that activate both may be pan-specific or act on off-target pathways common to both sensors whereas sensor specific hits are likely acting directly on the corresponding ppGalNAc-transferase. FIG. 1 (D) shows an example of Q values (Q=(R−RNeg)/SDNeg) for each compound (treatment at 10 μM for 6 h) using the average of duplicate MG/GFP ratios for the compound (R), the vehicle-only control (RNeg), and the standard deviation of the vehicle-only controls (SDNeg). The cut-off values of +3 and −2.5 are indicated (*). Also indicated are the values for the positive controls (T2Δglycan and T3Δglycan) and the structure of the indicated T3-specific hit (inset). FIG. 1 (E) shows values (% enzyme activity relative to vehicle-only controls) for 20 hits from the primary screen in the in vitro assay using purified ppGalNAc-T2 or T3 as a secondary screen. Compounds were present at 50 μM. Compound 1614 is T3Inh-1.

FIG. 3 (A, C, E, and G) show representative fluorescent emission spectra from 510-550 nm of lysates obtained from HeLa cells treated with T3Inh-1 for 24 h at 0, 10, or 20 μM. The cells were stained with the indicated lectin for 30 min just prior to analysis. FIG. 3 (B, D, F, and H) provide quantified average staining values for the indicated lectins (at 520 nm emission) and T3Inh-1 treatments (n=3±SEM).

FIG. 4 shows representative images of untreated or T3Inh-1 treated (6 h, 100) HeLa cells after fixation and staining with antibodies against the indicated ppGalNAc-transferase and the Golgi marker GPP130. Bar=10 μm.

FIG. 5 (A) shows a comparison of T2 and T3 sensor activation at the indicated concentrations of T3Inh-1 (n=3±SEM). MG/GFP ratio was determined for 20,000 cells by FACS and average value is plotted as percent of the positive control (i.e. the Δglycan version of each sensor). FIG. 5 (B) shows comparison of effect of the indicated concentrations of T3Inh-1 on in vitro glycosylation mediated by purified ppGalNAc-T2, ppGalNAc-T3, or ppGalNAc-T6. Values are averages expressed as percentage of the control "vehicle-only" reactions (n=6±SEM for ppGalNAc-T3, n=3±SEM for others). FIG. 5 (C and D) show in vitro assays carried out in the presence of 0, 7.5, or 15 μM T3Inh-1 at the indicated concentrations of peptide or UDP-GalNAc substrate. Values are averages expressed as percent of the control reactions with no inhibitor and saturating substrates (n=3±SEM). FIG. 5 (E) shows representative fluorescence spectra for T3Inh-1 alone or for purified ppGalNAc-T3 in the presence of the indicated concentrations of T3Inh-1. Note dose-dependent quenching of tryptophan fluorescence indicating direct binding. FIG. 5 (F) shows fluorescence quenching quantified at each concentration using the peak value at 324 nm (n=3±SEM). Note that all graphs have error bars but some are too small to be apparent.

FIG. 6 (A) shows an example of cell migration through uncoated filters for the MDA-MB231 breast cancer cell line grown in the absence or presence of 5 μM T3Inh-1. The raw image of the filter shows both cells and the filter holes whereas a size-cut off was used in the thresholded image to specifically visualize the cells. Results were quantified by counting cells that migrated to the underside of the filter and each experiment was normalized using the average determined for controls at 24 h (n=3±SEM). FIG. 6 (B) shows an identical analysis except that the filters were pre-coated with Matrigel so that the assay measures invasion not just migration and the 48 h control was used for normalization (n=3±SEM). FIG. 6 (C) shows an example of MDA-MB231 proliferation determined for cells grown in the presence or absence of 5 μM T3Inh-1 by cell counting at 24 or 48 h. Representative images before and after thresholding (no size cutoff) are shown as well as quantification normalized by the value determined for untreated cells at 48 h (n=3±SEM). FIG. 6 (D) shows an example of mock and ppGalNAc-T3 transfected MCF7 cells plated on Matrigel-coated filters in the absence or presence of 5 μM T3Inh-1 for 24 h. Thresholded images show cells on underside of filters. Cell counts are shown relative to untreated controls after normalization using the total number of cells (determined using parallel wells 24 h post-plating). For all panels, asterisks denote p<0.05 (two-tailed Student's t test) for untreated to T3Inh-1 comparison.

FIG. 7 (A and B) shows Kaplan-Meier curves comparing overall survival (A) and metastasis-free survival (B) in patients with breast cancer between groups with high or low expression of ppGalNAc-T3. FIG. 7 (C) provides examples of immunoblots of cell lysates from the indicated cell types [HEK, HEKΔT3 (edited to lack ppGalNAc-T3 expression), MDA-MB231, MCF7, and MCF7-T3 (transfected to overexpress ppGalNAc-T3)] using anti-ppGalNAc-T3 and anti-tubulin antibodies.

FIG. 8 (A) shows an immunoblot of media collected from cells after a 6 h period in the presence of the indicated concentrations of T3Inh-1. HEK cells were transfected with FLAG-FGF23 and ppGalNAc-T3 or Myc-ANGPTL3 and anti-FLAG and anti-Myc antibodies were used to assay intact (*) and cleaved (<) FGF23 and ANGPTL3, respectively. The identity and origin of the unmarked band (at approximately 25 kD) is unknown and its presence was variable. FIG. 8 (B) provides an example of quantified results showing the percent ratio change of cleaved/intact FGF23 or ANGPTL3 normalized to the amount present in untreated controls (n≥3±SEM). FIG. 8 (C) shows examples of serum ELISA assay results showing ratio of cleaved/intact FGF23 in mouse sera collected 24 h after either 1 or 2 (consecutive day) intraperitoneal injections of the indicated amount of T3Inh-1 (averages of 4 animals±SEM). P-values are from two-tailed Student's t test.

FIG. 9 (A) shows a representative blot of recovery of intact (*) and cleaved (>) FGF23 in the media collected from cells after a 6 h period in the presence of the indicated concentrations of T3Inh-1. Unmarked bands here and in FIG. 9 (C and E) were considered background because they were absent for untransfected cells. FIG. 9 (B) provides quantified results for FGF23 in the media showing the relative amounts of each band (intact and cleaved) as a percent of the total (intact+cleaved for the untreated controls). Values are averages (n=3±SEM). FIG. 9 (C and D) shows panels identical to FIG. 9 (A and B) except that cell extracts were analyzed rather than cell media. FIG. 9 (E) shows example of recovery of intact (*) and cleaved (>) FGF23 in HEK cell extracts from cells treated with the indicated concentrations of T3Inh-1 for 6 h in the absence or presence of 100 μM chloroquine.

FIG. 10 provides a nucleic acid sequence (SEQ ID NO: 1), sequences of the furin cleavage linker sequences GLY (SEQ ID NO: 2) and ΔGLY (SEQ ID NO: 3), and an amino acid sequence of the complete ppGalNAc-T1 biosensor protein (SEQ ID NO: 4), with amino acids 61-186 of SEQ ID NO: 4 corresponding to the FAP HL4 serving as a blocking domain, amino acids 216-332 of (SEQ ID NO: 4) corresponding to the FAP mL5, amino acids 373-399 of (SEQ ID NO: 4) corresponding to the transmembrane domain, and amino acids 404-640 of (SEQ ID NO: 4) corresponding to the Venus fluorescent protein domain.

FIGS. 11A and 11B provide exemplary FAP sequences useful for binding and activating activatable malachite green compounds (SEQ ID NOS: 5-11, respectively).

FIGS. 12A-12C provide structures of exemplary activatable malachite green compounds, including malachite green (FIG. 12A) and MG-11p (FIG. 12C).

DETAILED DESCRIPTION

Figure 1A:
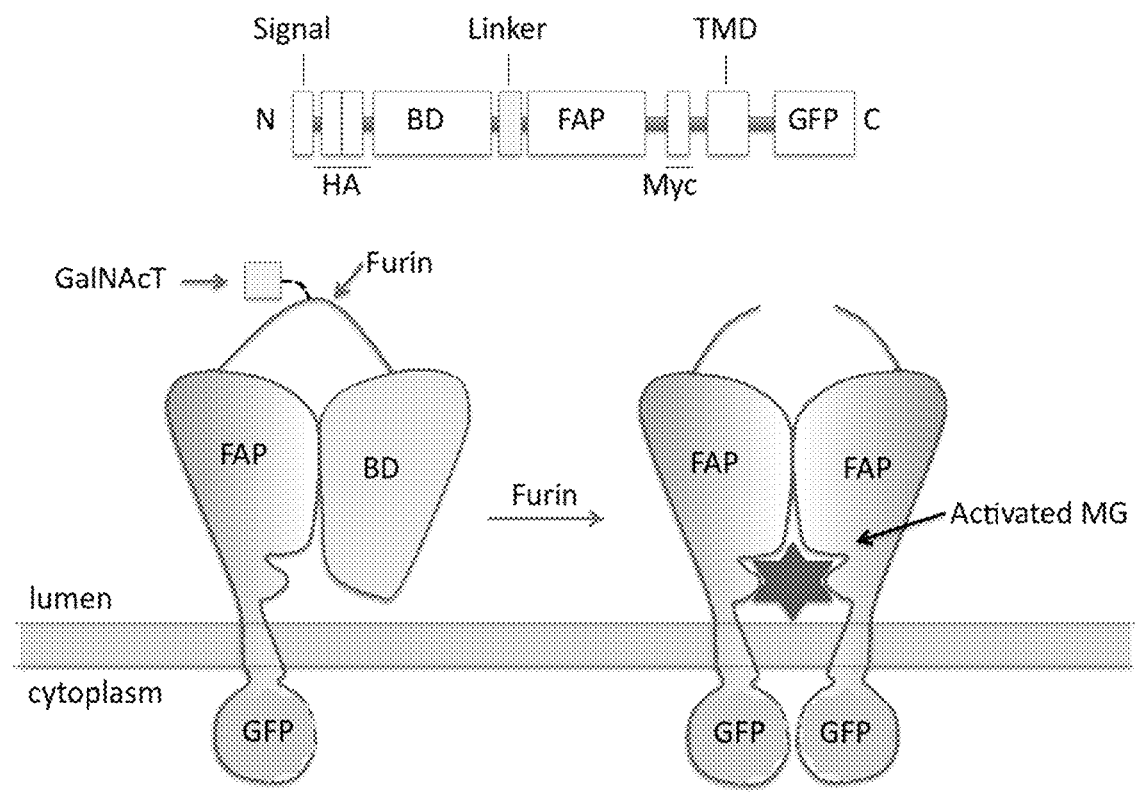
FIGS. 1A-1E provide an example of screening for modulators of ppGalNAc-T2/T3.
Figure 1B:
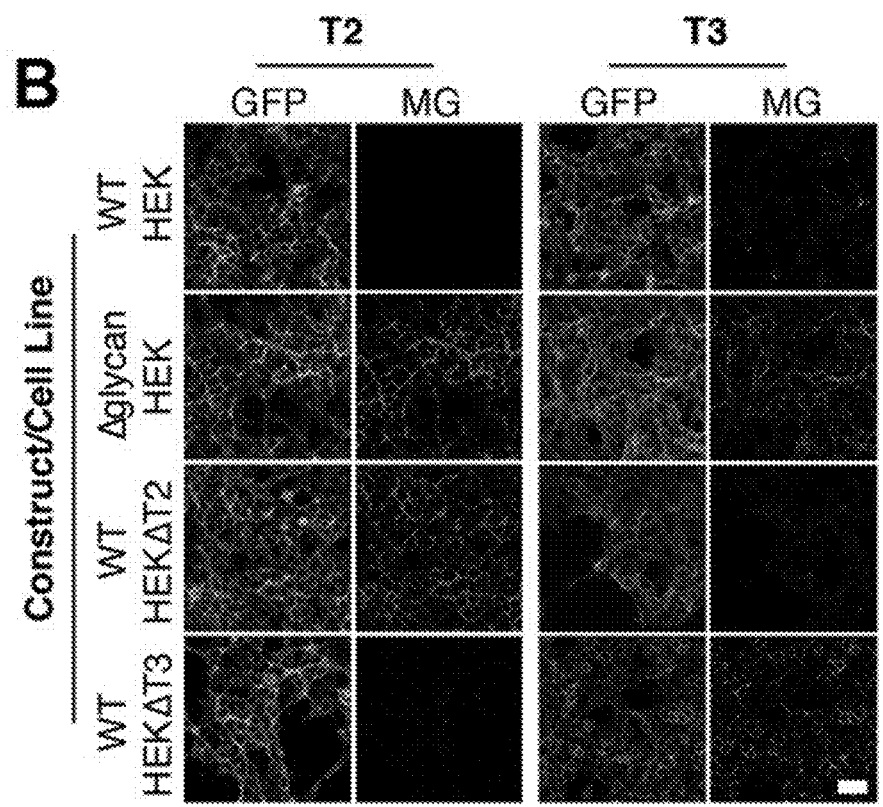
Figure 1C:
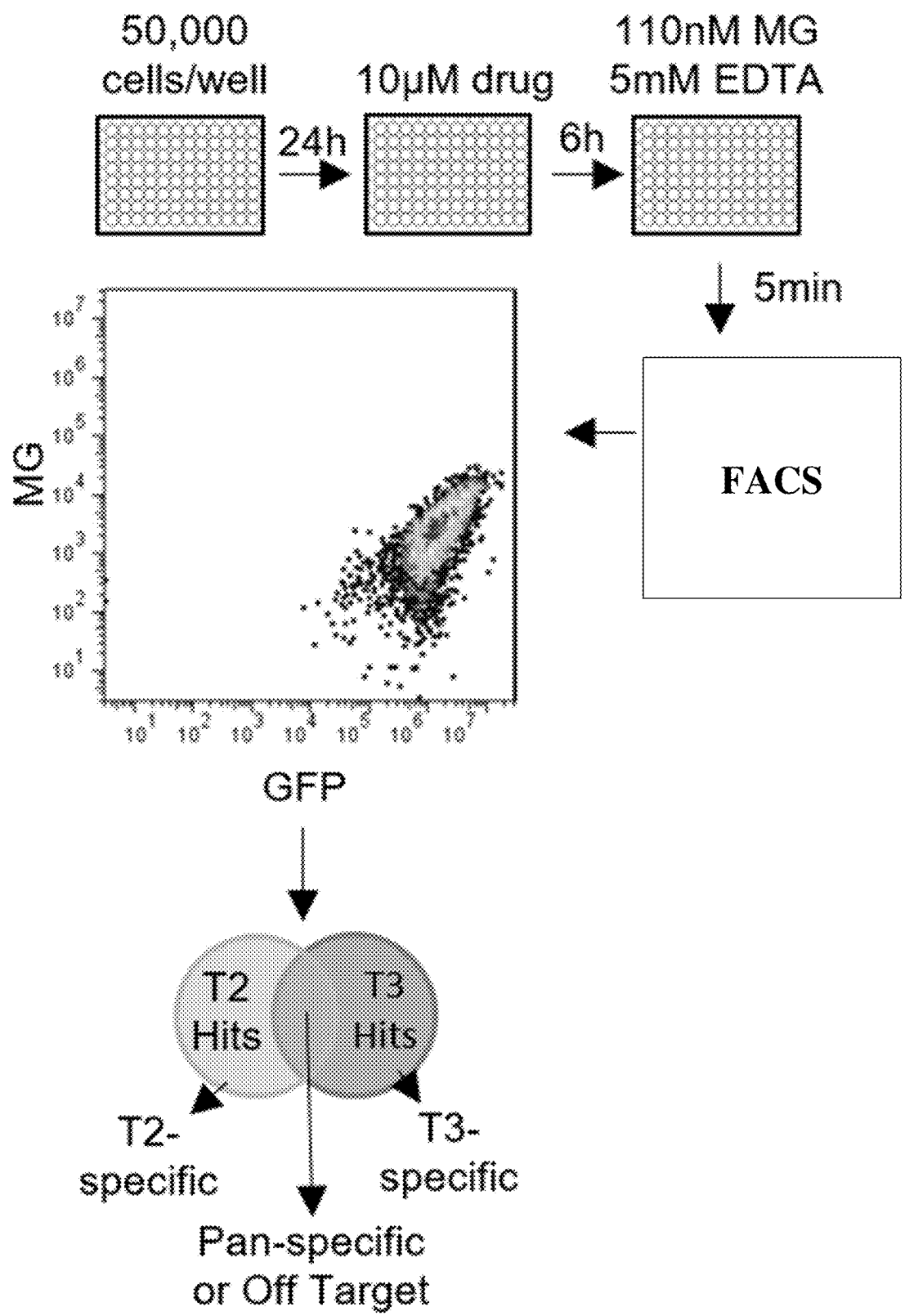
Figure 1D:
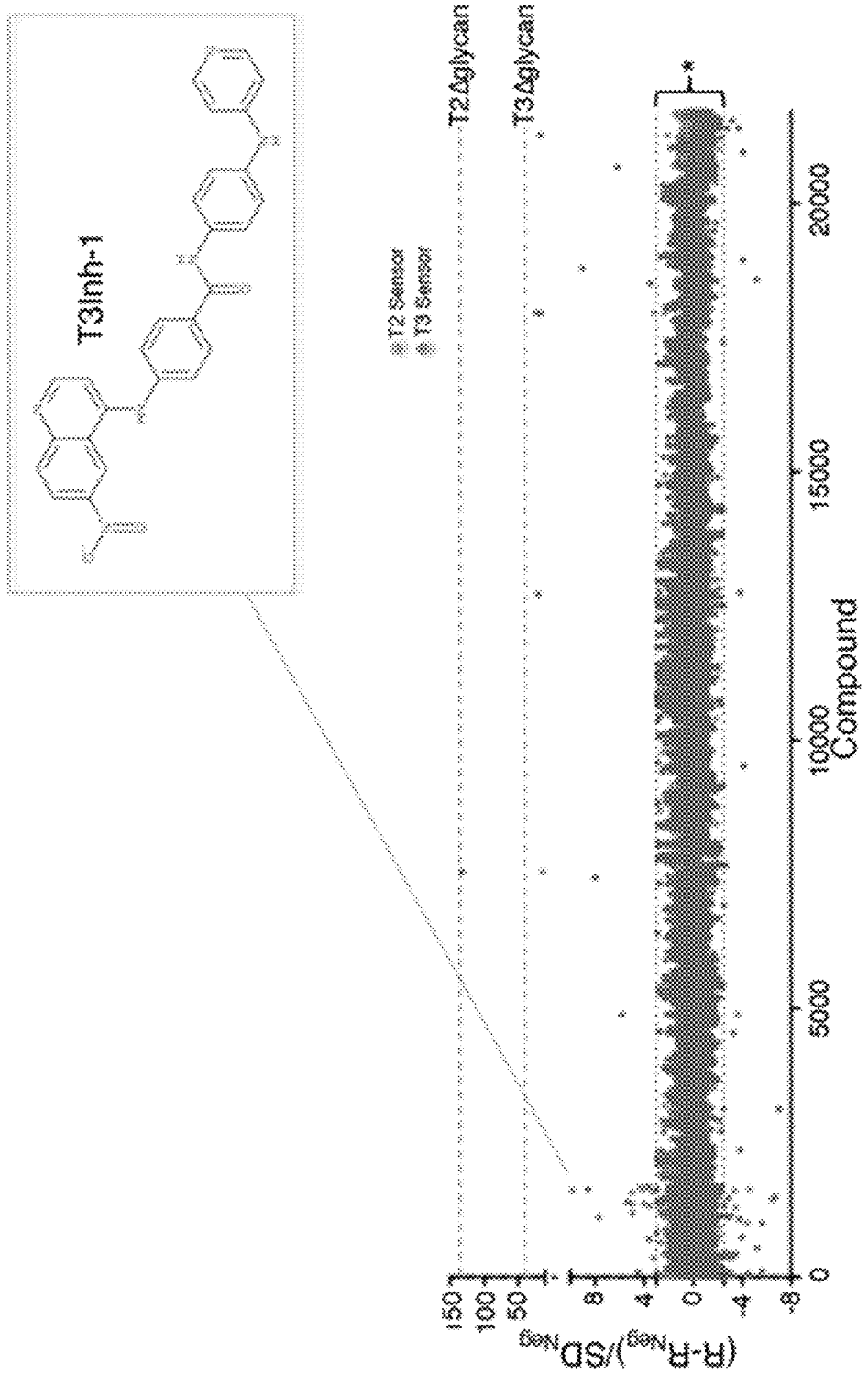
Figure 1E:
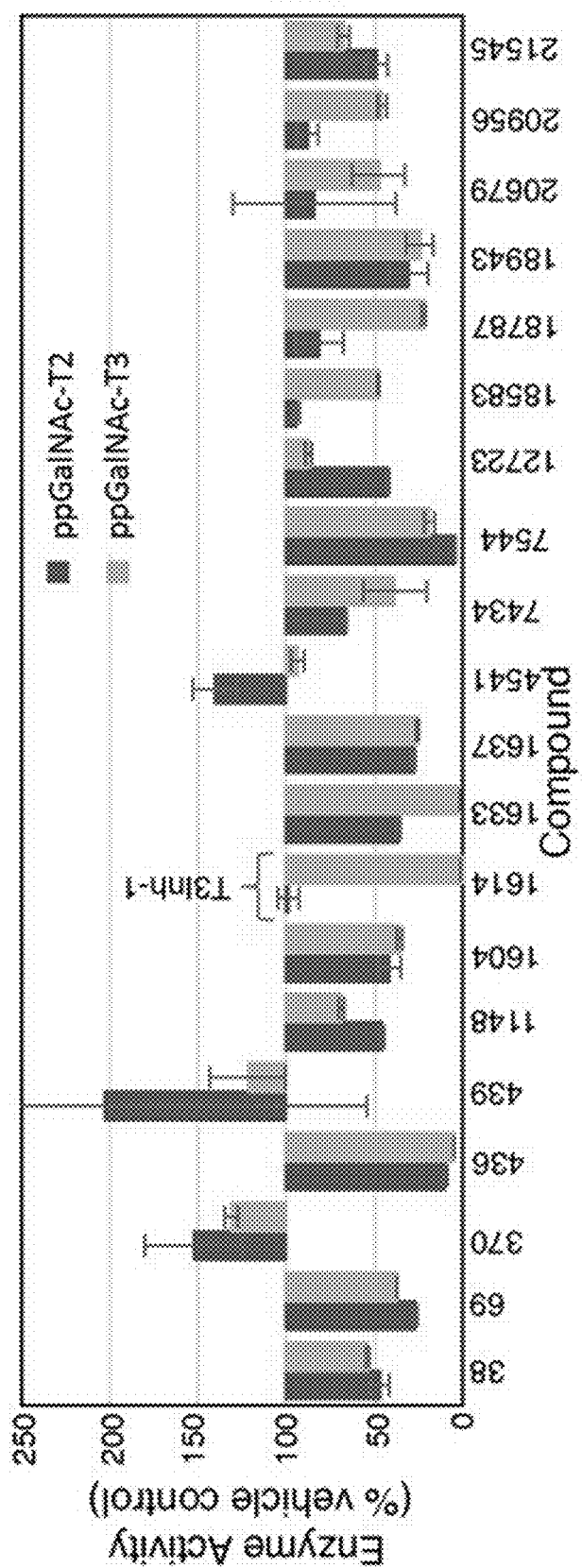

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the terms "comprising," "comprise" or "comprised," and variations thereof, are open ended and do not exclude the presence of other elements not identified. In contrast, the term "consisting of" and variations thereof is intended to be closed and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" a disease in which 0-glycosylation by the polypeptide N-acetylgalactosaminyltransferase in the Golgi complex is perturbed means administration to a patient, by any suitable dosage regimen, procedure and/or administration route, a composition, device or structure with the object of achieving a desirable clinical/medical end-point, including but not limited to, inhibiting site-specific O-glycosylation. In the context of chronic kidney disease, treatment will result in improved kidney function, such as an improvement (increase) in glomerular filtration rate (GFR) or an improvement (decrease) in urine albumin levels or in urine albumin-to-creatinine ratio (UACR). Treatment of cancer includes reducing growth rate of cancer cells, reduced tumor size, reduction of cancer metastatic potential or invasiveness, cancer remission, or any marker or symptom characteristic of the cancer.

Pharmaceutical compositions comprising an inhibitor of site-specific O-glycosylation may be prepared by any method known in the art of pharmacy, for example by bringing into association the active ingredient with the carrier(s) or excipient(s). As used herein, "carrier" or "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition.

Pharmaceutically acceptable carriers may further comprise minor amounts of auxiliary substances such as wetting or emulsifying agents, preservatives or buffers, which enhance the shelf life or effectiveness of the inhibitor of site-specific O-glycosylation. In certain embodiments, the active compound may be prepared with a carrier that will protect the compound against rapid release, such as a controlled release formulation, including implants, transdermal patches, and microencapsulated delivery systems. Biodegradable, biocompatible polymers can be used in preparation of a drug product, for example as a controlled-release composition for a therapeutic agent, such polymers include, without limitation, ethylene vinyl acetate, polyanhydrides, polyglycolic acid, collagen, polyorthoesters, and polylactic acid. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts. Many methods for the preparation of such formulations are patented or generally known to those skilled in the art.

"Pharmaceutically acceptable salts" are, because their solubility in water is greater than that of the initial or basic compounds, particularly suitable for medical applications. These salts have a pharmaceutically acceptable anion or cation. In addition, exchange chromatography can be used to change the counterion of the composition. Suitable pharmaceutically acceptable acid addition salts include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from the described compounds by any useful method, as are well known in the chemistry and pharmaceutical arts.

Additionally, compositions containing inhibitors of site-specific O-glycosylation may be in a variety of forms. The preferred form depends on the intended mode of administration and therapeutic application, which will in turn dictate the types of carriers/excipients. Suitable forms include, but are not limited to, parenteral, liquid, semi-solid and solid dosage forms.

Pharmaceutical formulations adapted for oral administration may be presented, for example and without limitation, as discrete units such as capsules or tablets; powders or granules; solutions or suspensions in aqueous or non-aqueous liquids; edible foams or whips; or oil-in-water liquid emulsions or water-in-oil liquid emulsions. In certain embodiments, the inhibitors of site-specific O-glycosylation may be contained in a formulation such that it is suitable for oral administration, for example, by combining an inhibitor of site-specific O-glycosylation with an inert diluent or an assimilable edible carrier. The compound (and other ingredients, if desired) may also be enclosed in a hard- or soft-shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical formulations adapted for transdermal administration may be presented, for example and without limitation, as discrete patches intended to remain in intimate contact with the epidermis of the recipient for a prolonged period of time or electrodes for iontophoretic delivery.

Pharmaceutical formulations adapted for topical administration may be formulated, for example and without limitation, as ointments, creams, suspensions, lotions, powders, solutions, pastes, gels, sprays, aerosols or oils.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient. Pharmaceutical formulations adapted for administration by inhalation include, without limitation, fine particle dusts or mists which may be generated by means of various types of metered dose pressurized aerosols, nebulizers or insufflators.

Pharmaceutical formulations adapted for parenteral administration include aqueous and non-aqueous sterile injection solutions which may contain, for example and without limitation, anti-oxidants, buffers, bacteriostats, lipids, liposomes, emulsifiers, also suspending agents and rheology modifiers. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Therapeutic compositions typically must be sterile and stable under the conditions of manufacture and storage. For example, sterile injectable solutions can be prepared by incorporating the active compound (i.e., the inhibitor of site-specific O-glycosylation) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A "therapeutically effective amount" refers to an amount of an active ingredient, e.g., a drug, effective, at dosages and for periods of time necessary, to achieve a desired therapeutic result. An "amount effective" for treatment of a condition is an amount of an active agent, drug product, or dosage form effective to achieve a determinable end-point. The "amount effective" is preferably safe—at least to the extent the benefits of treatment outweighs the detriments and/or the detriments are acceptable to one of ordinary skill and/or to an appropriate regulatory agency, such as the U.S. Food and Drug Administration. A therapeutically effective amount of an inhibitor of site-specific O-glycosylation may vary according to factors such as the disease state, age, sex, and weight of the individual, and the ability of an inhibitor of site-specific O-glycosylation to elicit a desired response in the individual. A therapeutically effective amount is also one in which any toxic or detrimental effects of an inhibitor of site-specific O-glycosylation are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, every 10, 15, 20, 30, 45, 60, 90, or 120 minutes, every 2 through 12 hours daily, or every other day, etc. be proportionally reduced or increased as indicated by the exigencies of the therapeutic situation. In some instances, it may be especially advantageous to formulate parenteral compositions in dosage unit form for ease of administration and uniformity of dosage. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

By "expression" or "gene expression," it is meant the overall flow of information from a gene, to produce a gene product. A "gene" is, without limitation, a functional genetic unit for producing a gene product, such as RNA or a protein in a cell, or other expression system encoded on a nucleic acid and comprising: a transcriptional control sequence, such as a promoter and other cis-acting elements, such as transcriptional response elements (TREs) and/or enhancers;

an expressed sequence that typically encodes a protein (referred to as an open-reading frame or ORF) or functional/structural RNA, and a polyadenylation sequence. A "gene product" typically is a protein, optionally post-translationally modified, or a functional/structural RNA. A "Gene for expression of" a stated gene product, e.g. protein, means a gene capable of expressing a specific protein or functional RNA when transferred into a suitable cell.

Expression of a gene can be downregulated, that is lowering levels or activity of the gene product of the gene, for example by lowering transcription rates from the gene, reducing transcribed RNA levels, reducing or inhibiting post-transcriptional processing of the gene product, by enhanced degradation of the gene product thereby reducing the availability of the gene product, or by any other mechanism that renders the gene product less available or less active. Downregulation of a gene can be accomplished, for example and without limitation, pharmacologically by administering to a patient an inhibitor of gene expression, or by RNA interference. Likewise, expression of a gene can be upregulated, that is increasing levels of, or activity of, the gene product of the gene, for example by inducing or otherwise increasing transcription rates from the gene, by increasing RNA stability, by increasing post-transcriptional processing of the gene product, by reduced degradation of the gene product and thereby increasing the availability of the gene product, or by any other mechanism that renders the gene product more active or available. "Activity" of a gene product, such as an enzyme, refers to the overall ability of a gene product in a cell, tissue, or organism, to function, e.g. to catalyze a certain reaction, or to bind a binding partner such as a receptor, factor, protein, etc. Activity can be a function of expression of the gene product, or can be affected by extrinsic factors, such as, for example and without limitation, the presence of antagonists, agonists, cofactors; presence of or absence of substrate or product; presence of, absence of, or mutations in binding partners; and/or physical factors, such as pH or salt concentration.

A gene can be transferred into a cell, such as a eukaryotic or mammalian cell by any useful method. A gene transferred into a cell for expression in that cell is referred to herein as a "transgene", and is transferred in the form of a nucleic acid comprising the transgene. Often a transgene is introduced into a cell using an "expression vector", otherwise known as an "expression construct", which can be a recombinant plasmid or virus designed for gene expression in cells. Other methods, such as CRISPR-CAS or TALENS, may be used to introduce a transgene into a cell or cell line. The transgene can be integrated into the genome of a cell into which it is transferred, such as with Adeno-associated virus (AAV) transduction, or genomic editing. Alternatively, the transgene can be maintained episomally. The expression of a transgene protein may be tightly controlled, and the protein is only produced in significant quantity when necessary through the use of an inducer, in some systems however the protein may be expressed constitutively. Preparation of suitable transgenes and vectors for transfer of a transgene in a cell, as well as suitable gene transfer methods are broadly known in the molecular biology arts, and many cloning and gene transfer reagents and kits, e.g., for viral vector-mediated transfer, or for gene editing, are broadly-available. In the context of the sequences provided in FIG. 10, one of ordinary skill can readily prepare a cell line that expresses the protein depicted therein, and one of ordinary skill can readily generate and test other described sensor constructs as described herein, e.g. with different FAP sequences. Due to the modular nature of the sensor construct of FIG. 10, other sensors as described herein are generally expected to function in a similar manner.

Expression vectors compatible with eukaryotic cells, preferably those compatible with vertebrate cells, can be used to produce recombinant constructs for the expression of a sensor as described herein. Eukaryotic cell expression vectors are well known in the art and are available from a number of commercial sources. Typically, such vectors are provided containing convenient restriction sites for insertion of the desired nucleic acid segment.

Viral vector systems which can be utilized with the methods and compositions described herein include, but are not limited to: (a) adenovirus vectors; (b) retrovirus vectors, including, but not limited to, lentiviral vectors, moloney murine leukemia virus, etc.; (c) adeno-associated virus (AAV) vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g., canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g., EPV and EBV vectors. Constructs for the recombinant expression of a sensor as described herein will generally require regulatory elements, e.g., promoters, enhancers, etc., to ensure the expression of the sensor in target cells. Other aspects to consider for vectors and constructs are known in the art.

"Transfection" is the process of deliberately introducing naked or purified nucleic acids into eukaryotic cells. "Transformation" is typically used to describe non-viral DNA transfer in bacteria and non-animal eukaryotic cells, including plant cells. "Transduction" is often used to describe virus-mediated gene transfer into eukaryotic cells.

A "Fluorescent protein" is a protein that will fluoresce when exposed to light in its excitatory spectrum. Non-limiting examples of fluorescent proteins include green-fluorescent protein, yellow fluorescent protein, and red fluorescent protein, and includes derivatives of these proteins, such as the modified yellow fluorescent protein "Venus", as described in the examples. A large variety of fluorescent proteins are available in the relevant arts and commercially, see, e.g., Lambert, T J (2019) FPbase: a community-editable fluorescent protein database. See, e.g., Nature Methods. doi: 10.1038/s41592-019-0352-8 and Cranfill, P J, et al., "Quantitative Assessment of Fluorescent Proteins" Nat Methods. 2016 July; 13(7): 557-562.

A "Transmembrane Domain" is a generally hydrophobic domain of a protein that typically serves to anchor and orient the protein in a cell membrane, e.g., a transmembrane segment of single alpha helix of a transmembrane protein. Transmembrane domains may traverse a lipid bilayer more than once. The transmembrane domain shown in FIG. 10 is merely exemplary and one of ordinary skill can choose suitable transmembrane domain sequences, for example, either based on the sequence provided in FIG. 10, based on sequences of non-polar or hydrophobic amino acids or amino acid sequences, using any of the available bioinformatics resources configured to predict or locate transmembrane sequences, or based on identified transmembrane sequences as are broadly known in the art.

"Fluorogen-activating proteins" (FAPs) include single chain variable fragment (scFv) molecules that are specific for nonfluorescent organic dye molecules, and which cause these dyes to be fluorescent only when they are bound to the protein module in the presence of free dye in solution. Using clones of high affinity (low nanomolar), this binding survives many wash steps, while with clones of low affinity (micromolar), the presence of the dye is required to maintain fluorescence signal. scFv modules are available in yeast display libraries and other display libraries, which can be used to generate specific binding partners for a wide variety of molecules and proteins. One advantage of this genetically encoded system is that the selected antibodies, or dimers thereof can be used as expressible protein tags. This allows a relatively small unit (typically ~25 kDa molecular weight for a "whole" scFv, or as small as 11 kDa for a "single domain" scFv) to be expressed as a fusion protein with a specific partner in the cellular context, though the scFv can be attached to a specific partner, such as a cellular protein, ligand, receptor, antibody, etc. by any effective means.

Exemplary FAP domains include HL4, mL5 or similar domains as described, for example and without limitation, in: Falco C N, et al. "scFv-based fluorogen activating proteins and variable domain inhibitors as fluorescent biosensor platforms." Biotechnol J 2009; 4:1328-1336; Szent-Gyorgyi C, et al. "Fluorogen-activating single-chain antibodies for imaging cell surface proteins." Nat Biotechnol 2008; 26:235-240; Saunders, M G, et al. Fluorogen activating proteins in flow cytometry for the study of surface molecules and receptors, Methods Volume 57, Issue 3, July 2012, Pages 308-317, US 20120058494 A1, US 20110159519 A1, US 20130244891 A1 each of which is hereby incorporated by reference in its entirety.

An "activatable fluorogen" or "activatable fluorochrome" exhibits enhanced fluorescence when bound by (interacts with) the activator, e.g., the fluorescent activator protein. An example of such a fluorogen is a non-rigidized aromatic system, including monomethine dyes, cyanine dyes, malachite green, indocyanine green, acetylenic malachite green, dimethylindole red, a triarylmethine dye; a diarylmethine dye; and a monomethine dye.

Figure 12A:
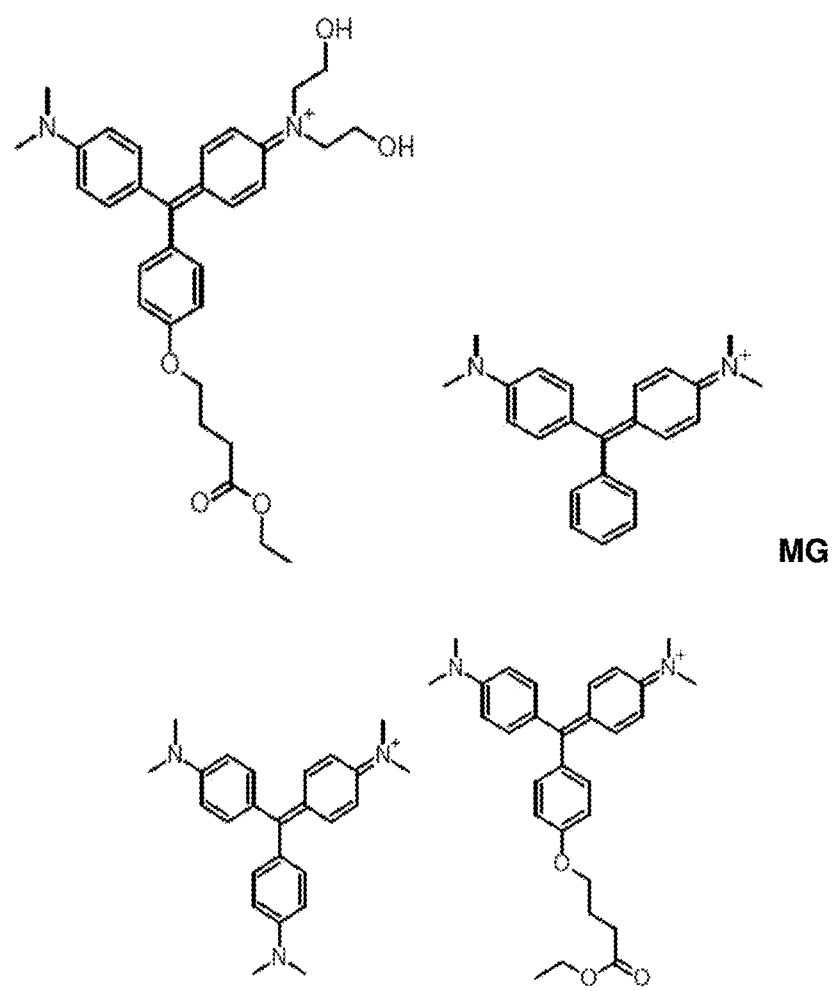
Figure 12C:
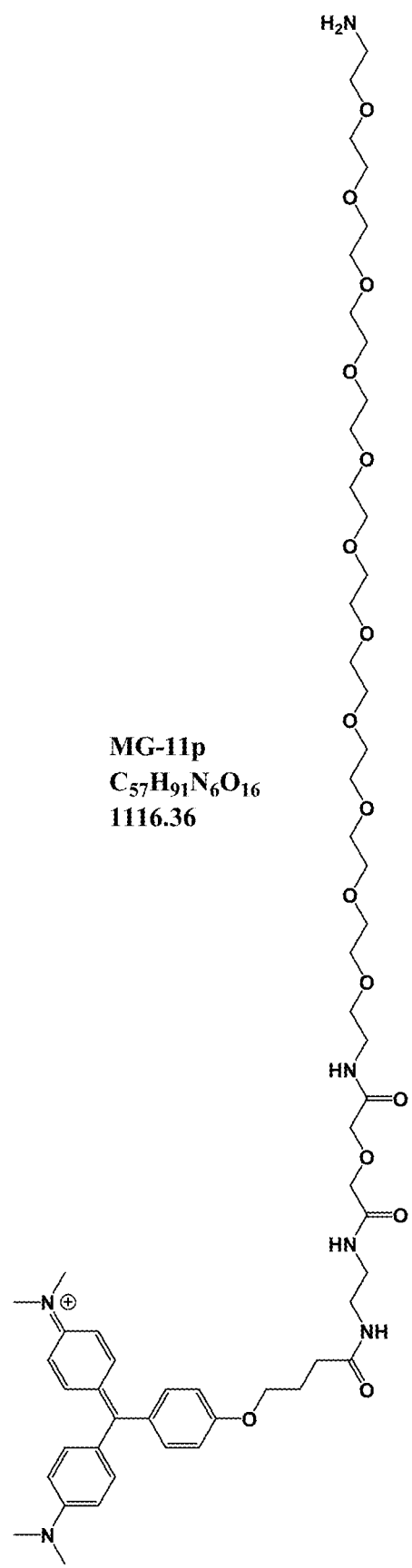

In one example, the activatable fluorogen is an activatable malachite green compound comprising a malachite green moiety, e.g., a residue having the general structure:

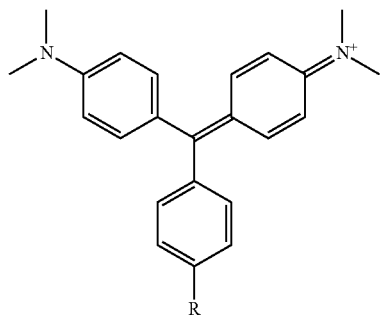

where R is a pendant group that does not interfere with the activation of the malachite green moiety by an FAP, e.g., as described herein, and the remainder of the structure is referred to herein as a malachite green moiety (see, MG in FIG. 12A for the structure of the malachite green cation). One or both of the methyl groups of the two nitrogen atoms of the malachite green moiety may be, independently, substituted with an ethyl, propyl, ethanol, or propanol group (see, e.g., FIG. 12A). Non-limiting examples of activatable malachite green moieties are described in Falco C N, et al. "scFv-based fluorogen activating proteins and variable domain inhibitors as fluorescent biosensor platforms." Biotechnol J 2009; 4:1328-1336; Szent-Gyorgyi C, et al. "Fluorogen-activating single-chain antibodies for imaging cell surface proteins." Nat Biotechnol 2008; 26:235-240; Saunders, M G, et al. Fluorogen activating proteins in flow cytometry for the study of surface molecules and receptors, Methods Volume 57, Issue 3, July 2012, Pages 308-317, US 20120058494 A1, US 20110159519 A1, US 20130244891 A1, each of which is incorporated herein by reference in its entirety, and include the structures of FIGS. 12A-12C. In one example, R is a PEGylated moiety (a moiety comprising a poly(ethylene glycol) moiety (—(O—CH$_2$—CH$_2$)$_n$—), where n ranges from 2 to 1,000, e.g., R has the structure —O—(CH$_2$)$_3$—C(O)—NH—CH$_2$—CH$_2$—NH—C(O)—CH$_2$—O—CH$_2$—C(O)—NH—CH$_2$—CH$_2$—(O—CH$_2$—CH$_2$)$_n$—NH$_2$ where n ranges from 2 to 25, and in one embodiment (MG-11p), n is 11, or R comprises the structure —O-polyamide/linker-PEG, or —O-polyamide/linker-PEG-NH$_2$, wherein the polyamide is a linear alkyl moiety comprising from 1 to 5 amide groups separated by $C_1$-$C_6$ alkylene (divalent alkyl) moieties, where one or more carbon of the $C_1$-$C_6$ alkylene moieties is substituted with an O, and n for the PEG moiety ranges from 2 to 25. PEGylated malachite green compounds, e.g., as described, and in reference to MG-11p, are generally cell-impermeable. The —O-polyamide moiety is a non-limiting example of an inert linking group used to attach the PEG moiety to the malachite green moiety. Any inert linker/linking moiety can be substituted and can depend on the chemistry used to attach the PEG moiety to the malachite green moiety. By "inert" it is meant that the linker does not substantially interfere with the ability of the activatable malachite green compound to function in the context of the methods described herein. By "moiety" it is meant to be a part of a chemical compound. In one example, a moiety can be a monomer residue in a polymer, such as an acrylamide residue incorporated into a polyacrylamide polymer. FIGS. 12A-12C provide examples of activatable malachite green compounds, including MG-11P depicted in FIG. 12C.

GALNT1 or GALNAC-T1 (Entrez Gene ID: 2589), GALNT2 or GALNAC-T2 (Entrez Gene ID: 2590), and GALNT3 or GALNAC-T3 (Entrez Gene ID: 2591) are genes that encode members of the UDP-N-acetyl-alpha-D-galactosamine:polypeptide N-acetylgalactosaminyltransferase (GalNAc-T or also referred to as ppGalNAc-T) family of enzymes. GalNAc-Ts initiate mucin-type O-linked glycosylation in the Golgi apparatus by catalyzing the transfer of GalNAc to serine and threonine residues on target proteins. They are characterized by an N-terminal transmembrane domain, a stem region, a lumenal catalytic domain containing a GT1 motif and Gal/GalNAc transferase motif, and a C-terminal ricin/lectin-like domain. GalNAc-Ts have different, but overlapping, substrate specificities and patterns of expression.

In one aspect, provided herein are fluorescent biosensors capable of identifying modulators of ppGalNAc-T1, T2, and T3. A modulator of ppGalNAc-T1, T2, or T3 either up-regulates expression or activity of ppGalNAc-T1, T2, or T3. The sensors described herein detect O-glycosylation events based on a furin protease sensor that traffics through the secretory pathway. The furin sensor has a furin cleavage consensus site in a linker that connects a blocking domain (BD) to a fluorescence activating protein (FAP) domain (diagrammed in FIG. 1 (A)). When the linker is intact, the blocking domain prevents the FAP domain from binding and activating the dye malachite green (MG) or an activatable malachite green compound. Immediately adjacent to the furin site is a minimal consensus sequence for O-glycosylation (ppGalNAc isozyme-specific or pan-specific) so that O-glycosylation would block the access of furin. Thus, only non-glycosylated sensor molecules are cleaved by furin and become fluorescent. Additionally present in the sensor is the placement of a Venus fluorescent protein domain—a variant of yellow fluorescent protein or a Green Fluorescent Protein (GFP) in the cytoplasmic domain, allowing for localization and detection of the sensor regardless of its activation status.

Stated differently, the sensor provided herein is a polypeptide comprising at least the following linked domains: a blocking domain, a furin cleavage linker sequence, an FAP, a transmembrane domain, and, optionally, a fluorescent protein domain. Each domain is linked to form a contiguous polypeptide. The linkers used to join the various domains, if not directly linked without intervening amino acids, are "inert" in that they do not interfere to any substantial extent with the function of the construct as a sensor as described herein. The linkers are small, if present, having a length of no more than 10, 15, 20, or 25 amino acids. Non-limiting examples of useful linkers include poly-glycine (G) and GS linkers, e.g., of from 5-20 amino acids, such as GGGGS (SEQ ID NO: 12), GGGGSGGGGS (SEQ ID NO: 13), or GGGGSGGGGSGGGGS (SEQ ID NO: 14). All amino acid sequences are represented by standard one-letter codes and are recited in an N-terminal to C-terminal order. Despite being inert in the context of use of the sensor as described herein, the linkers may have a function, such as the HA-tag or MYC-tag sequences present in the sensor of FIG. 10. Linkers can have a variety of amino acid sequences and lengths so long as they remain inert in the context of the described biosensors. A person of ordinary skill can readily devise such linkers or linker sequences without undue experimentation.

In one embodiment, provided herein are expression constructs encoding a sensor comprising the following linked domains: blocking domain, a furin cleavage linker sequence, an FAP, a transmembrane domain, and a fluorescent protein. A non-limiting example of a sensor for detection of ppGalNAc-T1 is provided in FIG. 10. FAPs are binding reagents that bind and rigidize malachite green and malachite green derivatives. Malachite green does not normally fluoresce, but when bound by an FAP, it becomes fluorescent. Exemplary FAP sequences are provided in FIG. 11 (SEQ ID NOS: 5-11). Exemplary publications disclosing various FAP sequences and activatable malachite green derivatives include: Falco C N, Dykstra K M, Yates B P, Berget P B. "scFv-based fluorogen activating proteins and variable domain inhibitors as fluorescent biosensor platforms." Biotechnol J 2009; 4:1328-1336; Szent-Gyorgyi C, Schmidt B F, Creeger Y, Fisher G W, Zakel K L, Adler S, Fitzpatrick J A, Woolford C A, Yan Q, Vasilev K V, Berget P B, Bruchez M P, Jarvik J W, Waggoner A. "Fluorogen-activating single-chain antibodies for imaging cell surface proteins." Nat Biotechnol 2008; 26:235-240; WO 2008/092041. As indicated in the Falco reference, noted above, FAPs that activate MG can also block activity of other FAPs when linked together in the same chimeric protein, e.g., by a flexible linker of from 5 to 25 amino acids. In the examples below, the FAP is mL5 and the blocking domain is the FAP HL4. In the context of the sensor, the FAP can comprise the amino acid sequence of an FAP of any one of SEQ ID NOS: 5-11, and the blocking domain can comprise the amino acid sequence of an FAP of any one of SEQ ID NOS: 5-11. In the ppGalNAc-T1 sensor depicted in FIG. 10, the ppGalNAc-T1-specific linker (furin cleavage linker sequence) comprises the amino acid sequence REDRVTGSYQ (SEQ ID NO: 2).

The biosensor polypeptide may be expressed by a gene comprising an open reading frame encoding the sensor protein, such as the nucleic acid provided in FIG. 10. The gene may be transferred into, and expressed in any cell line or cell type, e.g., the HEK cells described in the examples below.

In one aspect of the invention, a method of screening for inhibitors of ppGalNAc-T1 are provided, comprising exposing a cell expressing the sensor of FIG. 10, or a biosensor polypeptide comprising, in order: a blocking domain, a furin cleavage linker sequence comprising the amino acid sequence REDRVTGSYQ (SEQ ID NO: 2), an FAP, a transmembrane domain, and, optionally, a fluorescent protein domain, where the blocking domain and the FAP are chosen from a FAP of any one of SEQ ID NOS: 5-11, for example the FAP is mL5 and the blocking domain is the FAP HL4. In the method, the cells are contacted with an activatable fluorogen, e.g., malachite green or an activatable malachite green derivative (an activatable malachite green compound), and a compound or composition to be tested. If the compound or composition to be tested inhibits a ppGalNAc-T1, the furin recognition sequence of the sensor will remain exposed and furin will cleave the polypeptide, releasing the blocking domain from the sensor, permitting the FAP to bind the activatable malachite green compound. If the compound or composition to be tested does not inhibit a ppGalNAc-T1, the furin recognition sequence will be sterically blocked, and the blocking domain will not be cleaved from the sensor, resulting in the failure of the activatable malachite green compound to bind to the FAP. In embodiments, the fluorescent protein, such as VENUS, is included in the sensor, to provide a reference, control value for the number of sensors present in a given cell population, such as a population of cells in a well of a multi-well culture dish. The compound or composition to be tested can be titrated, e.g., by putting the cells expressing the sensor in multiple wells of a multi-well dish, and different concentrations or dilutions of the compound or composition to be tested in different wells, e.g., with positive and negative controls, thereby producing a quantitative assay for determining not only whether or not the compound can inhibit the GalNAc-T1 enzyme, but at what concentrations the compound or composition inhibits the GalNAc-T1 enzyme. One embodiment of the assay is described below in the context of the T2 and T3. Inhibitors of GalNAc-T1 are expected to be useful in treating ebola infection (see, e.g., Simon, E J, et al., "Site-specific glycosylation of Ebola virus glycoprotein by human polypeptide GalNAc-transferase 1 induces cell adhesion defects" Dec. 21, 2018 J. Biol. Chem. 293:19866-19873).

Mice lacking ppGalNAc-T1 are viable and even fertile despite defects in blood clotting and bone development. Other functions that involve ppGalNAc-T1 are basement membrane deposition and extracellular matrix remodeling. The best characterized ppGalNAc-T1-specific substrates are two heavily O-glycosylated proteins involved in bone deposition and remodeling, bone sialoprotein, and osteopontin. There are at least 55 other glycoproteins that specifically depend on ppGalNAc-T1 for their glycosylation, but the functional importance of their glycosylation is unknown. Altered expression of ppGalNAc-T1 occurs in many types of cancer and the resulting aberrant glycosylation has contributed to the metastatic phenotype.

Also provided herein are methods for treating chronic kidney disease, wherein treatment will result in improved kidney function, such as an improvement (increase) in glomerular filtration rate (GFR) or an improvement (decrease) in urine albumin levels or in urine albumin-to-creatinine ratio (UACR). Chronic kidney disease, also called chronic kidney failure, describes the gradual loss of kidney function, for instance, when the kidneys are unable to filter wastes and excess fluids from a patient's blood. The method comprises administering to a patient an amount of a GalNAc transferase-3 inhibitor effective to treat chronic kidney disease in a patient. In one embodiment, the GalNAc transferase-3 inhibitor is

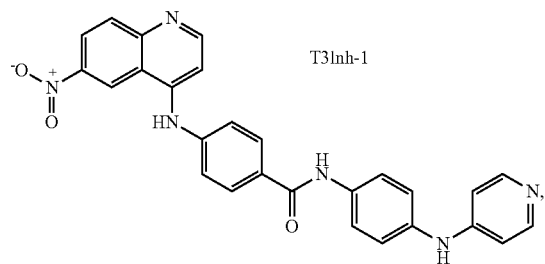

or a pharmaceutically-acceptable salt thereof ("T3Inh-1"). A therapeutically-effective amount of an inhibitor may range from 0.01-50 mg/kg (milligrams per kilogram of patient's weight), with an exemplary effective dose or a unit dose ranging from 10-25 mg/kg.

Provided herein also are methods for treating cancer including reducing growth rate of cancer cells, reduced tumor size, reduction of cancer metastatic potential or invasiveness, cancer remission, or any marker or symptom characteristic of the cancer. In some embodiments, provided herein are methods for treating or reducing the invasiveness of breast cancers. The method comprises administering to a patient an amount of a GalNAc transferase-3 inhibitor effective to treat cancer, e.g., breast cancer, in a patient. In one embodiment, the GalNAc transferase-3 inhibitor is

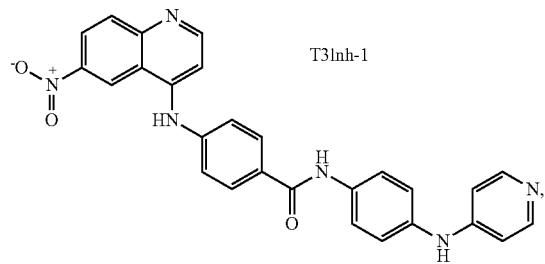

or a pharmaceutically-acceptable salt thereof ("T3Inh-1"). A therapeutically-effective amount of an inhibitor may range from 0.01-50 mg/kg, with an exemplary effective dose or a unit dose ranging from 10-25 mg/kg.

Further, provided herein are inhibitors of site-specific O-glycosylation. In one aspect, the inhibitors provided herein are non-competitive/mixed-mode inhibitors. By "non-competitive/mixed-mode", it is meant that the inhibitor is able to bind both freely-available enzyme as well as enzyme that is bound to its substrate. "Non-competitive/mixed-mode" refers to the mechanism of inhibition, it means it binds and inhibits both substrate-free and substrate-bound forms of ppGalNAc-T3. The method comprises administering to a patient an amount of a GalNAc transferase-3 inhibitor effective to inhibit site-specific glycosylation in a patient. In one embodiment, the GalNAc transferase-3 inhibitor is

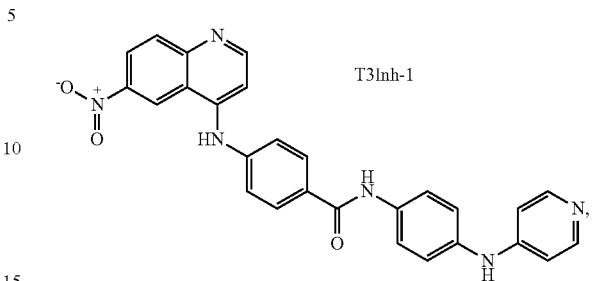

or a pharmaceutically-acceptable salt thereof ("T3Inh-1"). A therapeutically-effective amount of an inhibitor may range from 0.01-50 mg/kg, with an exemplary effective dose or a unit dose ranging from 10-25 mg/kg.

EXAMPLES

Small molecule inhibitors of site-specific O-glycosylation in the Golgi complex by the polypeptide N-acetylgalactosaminyltransferase (UDP-N-acetyl-α-D-galactosamine polypeptide N-acetyl-galactosaminyltransferases or ppGalNAc-T) family are currently unavailable but hold promise as therapeutics for major diseases, especially if selective against individual ppGalNAc-T isozymes.

For example, ppGalNAc-T3 has been implicated in at least two medically important pathways: cancer metastasis and stabilization of FGF23. ppGalNAc-T3 is overexpressed in cancerous tissue often correlating with shorter survival. Knockdown of ppGalNAc-T3 expression in cultured ovarian cancer cells inhibits their invasive capacities arguing that ppGalNAc-T3 has potential as a therapeutic target. ppGalNAc-T3 mediates glycan-masking of FGF23 in bone as part of a control mechanism determining the form of FGF23 that is secreted. When present, the added O-glycan blocks FGF23 cleavage by the furin protease resulting in secretion of intact FGF23 that activates FGF23 receptor complexes at the kidney and intestine. In contrast, non-glycosylated FGF23 is cleaved and the cleaved C-terminal product competitively blocks these same receptors. Significantly, elevated intact FGF23 occurs in chronic kidney disease and upon kidney transplant where it is directly linked to poor prognosis due to its effects on renal phosphate reabsorption and 1,25-dihydroxyvitamin D biosynthesis.

GalNAc-T3 regulates the endocrine hormone fibroblast growth factor-23 (FGF23) to control phosphate homeostasis. Elevated FGF23 causes hypophosphatemia, adversely affecting nearly every major tissue, and occurs in both chronic kidney disease (CKD) and upon kidney transplant where it is independently associated with mortality and morbidity. Work in animal models shows that FGF23 neutralization is effective but there are no drug-like materials available for this purpose. Inhibitors of GalNAc-T3 lower FGF23, and represent a novel therapeutic approach to hypophosphatemia and CKD.

Example 1

To enable high-throughput screening for small molecule modulators of GalNAc-Ts, we developed cell-based fluorescent sensors of O-glycosylation by modification of a sensor based on the malachite-green binding fluorescence activating protein domain. The sensors are either isozyme-specific or "pan"-specific. The former contain a glycan-acceptor site that is recognized by a single GalNAc-T isozyme (family members are termed T1-T20). The latter contain a universal acceptor sequence recognized by all or most family members. Sensor fluorescence increases upon GalNAc-T inhibition and decreases upon activation. They are ratiometric because the sensor backbone contains a green fluorescent protein as an internal control for expression. Importantly, simultaneous screening with two isozyme-specific sensors allows identification of sensor-specific modulators greatly increasing the chance of recovering direct rather than indirect hits.

To identify a compound targeting the ppGalNAc-T3 isozyme, we screened libraries to find compounds that act on a cell-based fluorescence sensor of ppGalNAc-T3 but not on a sensor of ppGalNAc-T2. We initiated screening using the T3- and T2-specific sensors and identified compounds (low molecular weight, reasonably water soluble, membrane permeant) that specifically inhibit (or activate). These: a) block (or activate) one cell-based sensor but not the other, b) block (or activate) the corresponding purified GalNAc-T in an in vitro assay (confirming that they are direct and specific), c) do not have apparent toxic effects on cultured cells, d) do not alter GalNAc-T cellular expression or localization, and e) do not perturb overall O-linked or N-linked glycosylation as determined using lectin staining.

One T3 inhibitor, a bis-quaternary salt of a quinolone (4-[p-(4-pyridylamino)phenylcarbamoyl)aniline]-quinoline) has been further characterized. It binds GalNAc-T3 with low micromolar affinity conferring a non-competitive/mixed mode of inhibition. Significantly, it enhances proteolysis of FGF23 both in cultured cells and after intraperitoneal injection of mice. In the latter case, the level of the proteolyzed, inhibitory, C-terminal FGF23 fragment increases by 8-fold showing the promise of the compound as a therapeutic approach to antagonize aberrant FGF23 signaling in CKD and other diseases.

HEK cell lines were engineered to express fluorescent sensors that are specific to ppGalNAc-T2 or ppGalNAc-T3 activity. For each sensor, glycosylation of its isozyme-specific target site prevents furin protease from removing a blocking domain (FIG. 1 (A)). Thus, fluorescence increases upon ppGalNAc-transferase inhibition because removal of the blocking domain allows dimerization of a fluorogen activating protein domain so that it binds and activates the fluorescence of malachite green. They are ratiometric because the sensor backbone contains a green fluorescent protein as an internal control for expression. Each sensor showed clear activation after mutation of its glycan acceptor sites and these mutated constructs served as positive controls in the screen (FIG. 1 (B), Δglycan). The T3 sensor exhibited a background level of activation due to incomplete glycosylation but this was considered advantageous for the possible identification of enzyme activators along with the desired inhibitors. Sensor expression in HEK cell lines depleted of either ppGalNAc-T2 or T3 via zinc finger nuclease editing resulted in specific activation of the corresponding sensor confirming their isozyme selectivity (FIG. 1 (B), HEKΔT2, HEKΔT3). Our screen included compounds based on structural diversity (21,710 compounds in total) with 6 h treatments at 10 μM prior to flow cytometry to assay MG and GFP fluorescence on a cell-by-cell basis (FIG. 1 (C). Each compound was tested in duplicate and against both sensors. Because each sensor requires essentially identical cellular reactions—the only difference being which ppGalNAc-transferase isoform modifies the sensor—most off-target hits (such as sugar nucleotide transporters, extending enzymes, or furin) will alter both sensors, whereas directly acting, isoform-specific candidates will be sensor-specific. Using cut-off parameters for the MG/GFP ratios that excluded >99% of the compounds (Q≥3 or Q≤2.5), the screen yielded 72 sensor-specific hits with 18 increasing and 35 decreasing the T2 sensor fluorescence and 11 increasing and 8 decreasing the T3 sensor fluorescence (FIG. 1 (D).

To determine which of these directly acted on the targeted enzymes, we carried out in vitro glycosylation assays in which the purified lumenal domains of ppGalNAc-T2 or ppGalNAc-T3 (containing catalytic and lectin domains) were incubated with peptide and UDP-GalNAc substrates in the presence of 50 μM of each compound. A second stage reaction (UDP-GLO™) then converted the accumulated UDP product to ATP and then, via luciferase, to light. This resulted in 20 candidates that either reduced or increased the luminescence by a factor ≥50% relative to vehicle-only controls (FIG. 1 (E). Of these, one compound (#1614) stood out as a strong and selective inhibitor of ppGalNAc-T3 and became the focus of this phase of the study. The compound is a quinoline of no known activity that we now refer to as ppGalNAc-T3 Inhibitor 1 or T3Inh-1 (FIG. 1 (D), inset).

Figure 2:
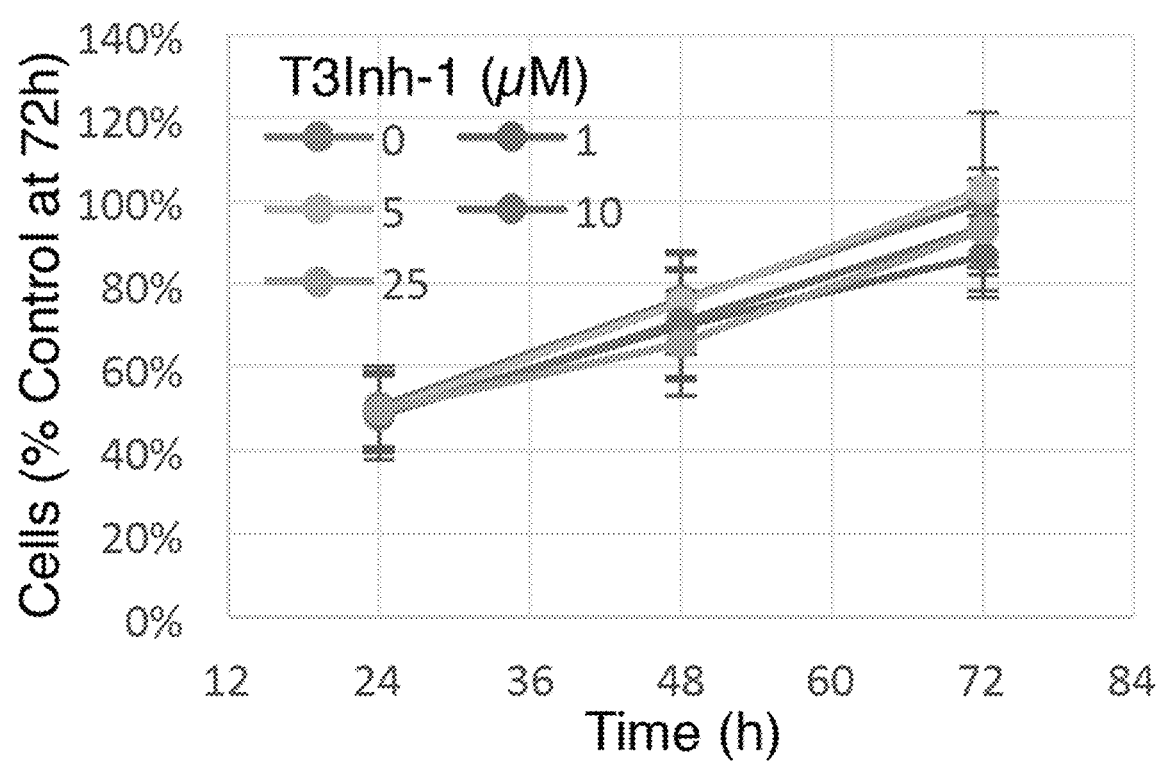
FIG. 2 presents an example of cell growth at various T3Inh-1 exposures. Identical numbers of HEK cells were plated and grown in the continuous presence of the indicated concentrations of T3Inh-1 and then at 24, 48, or 72 h they were released and counted. Averages are shown normalized using the untreated sample at 72 h (n=3±SEM).
Figure 3A:
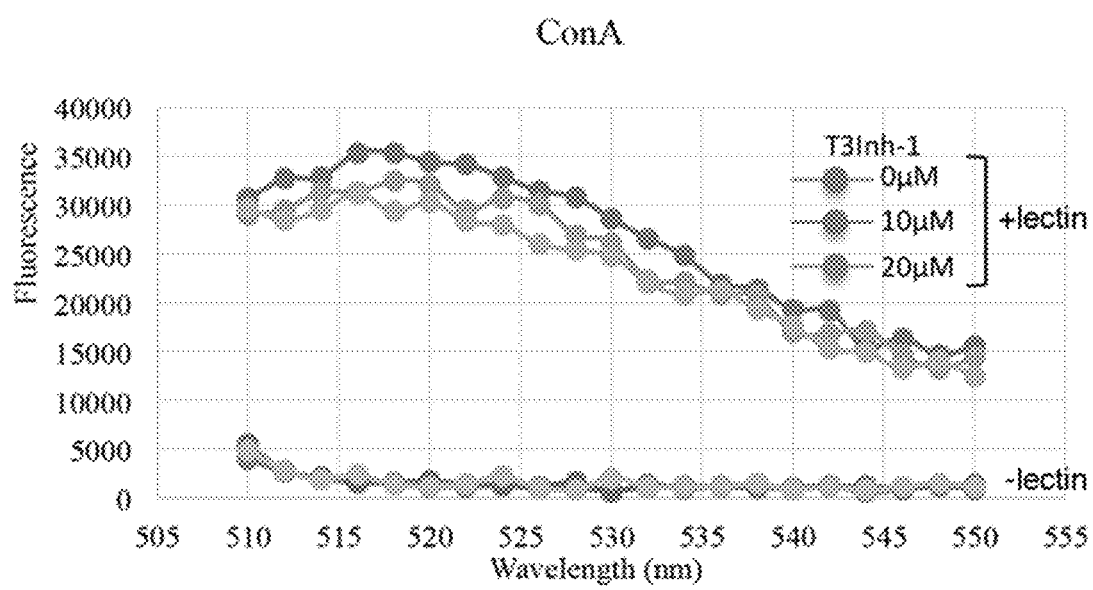
FIGS. 3A-3H show general N- and O-glycosylation are unaffected.
Figure 3B:
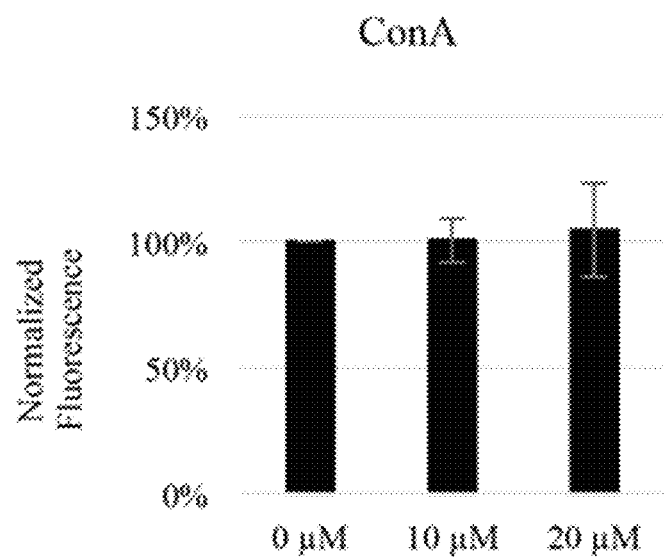
Figure 3C:
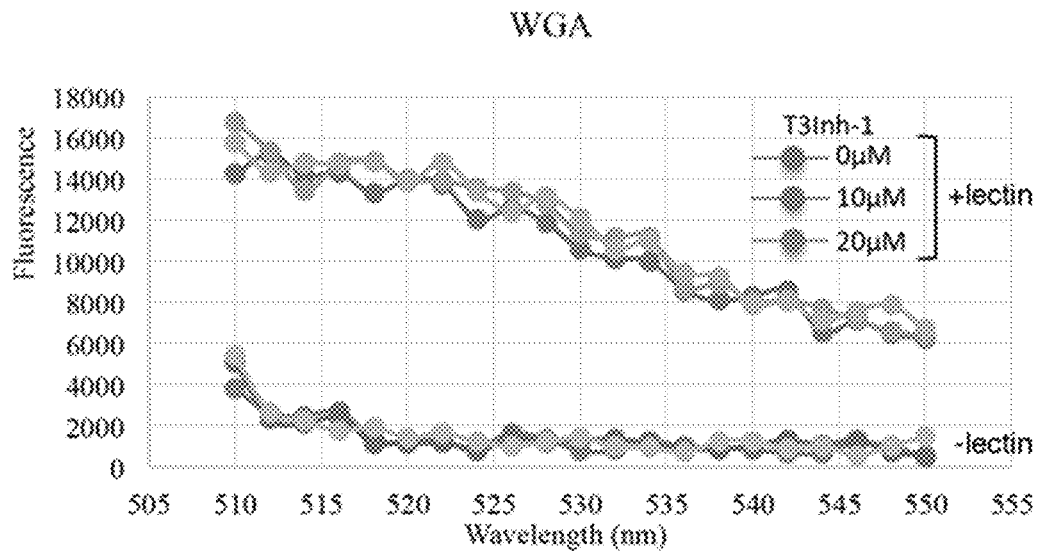
Figure 3D:
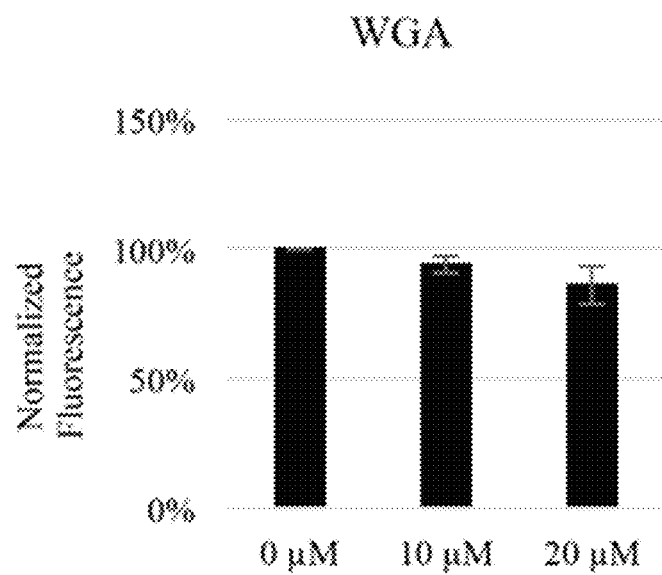
Figure 3E:
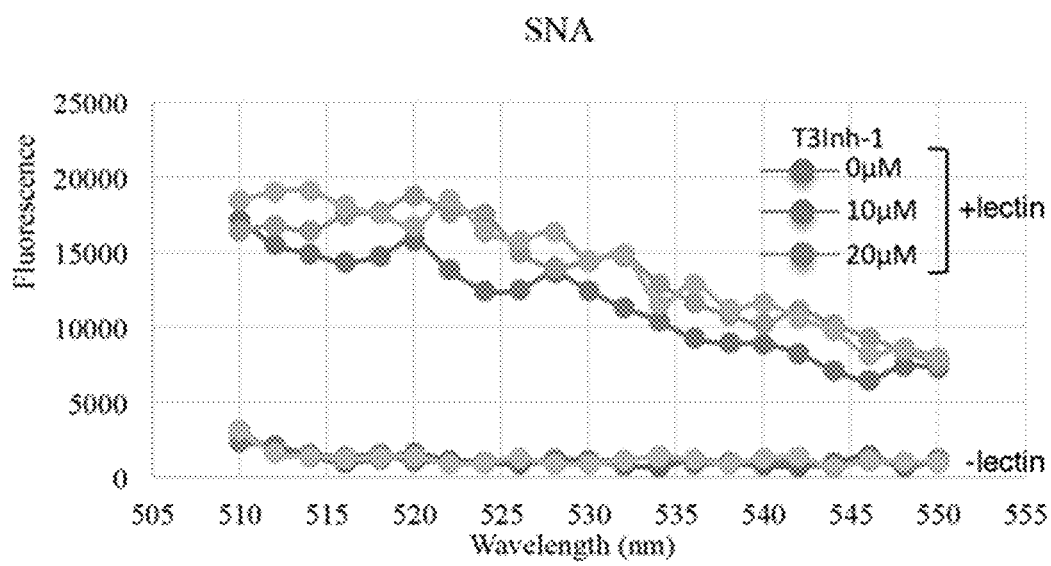
Figure 3F:
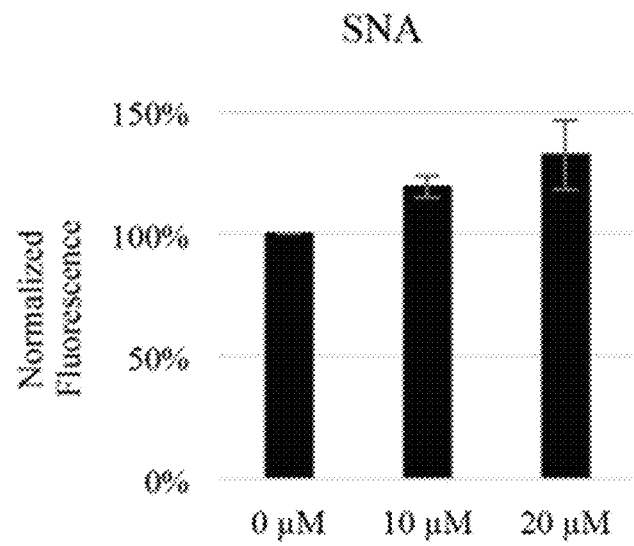
Figure 3G:
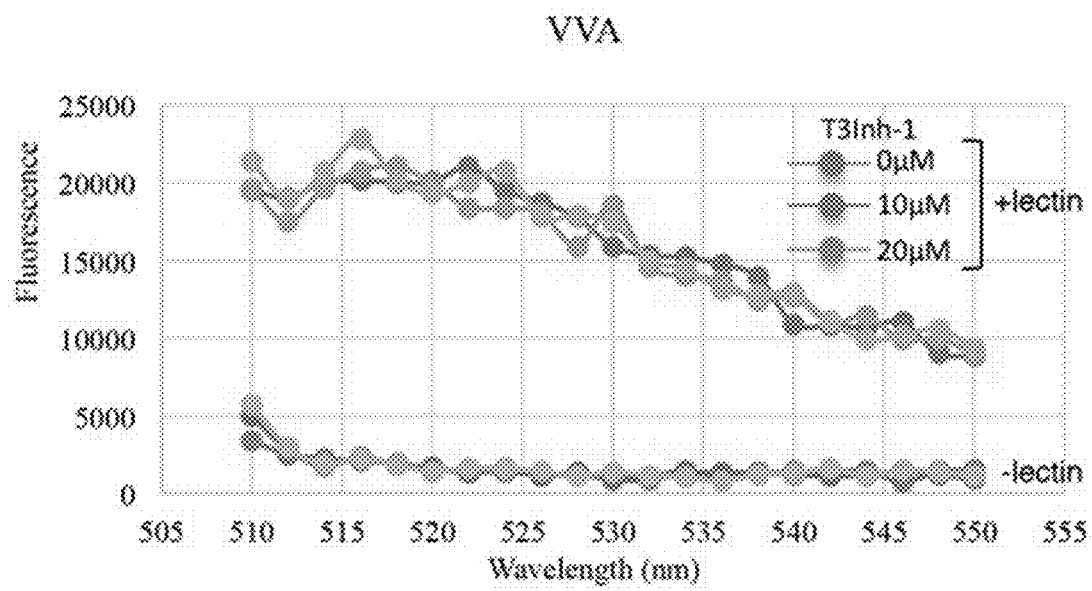
Figure 3H:
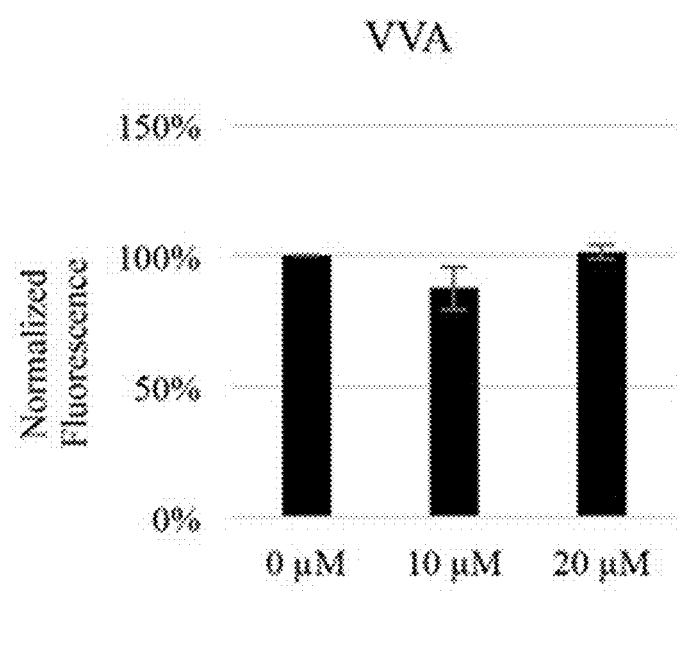
Figure 4:
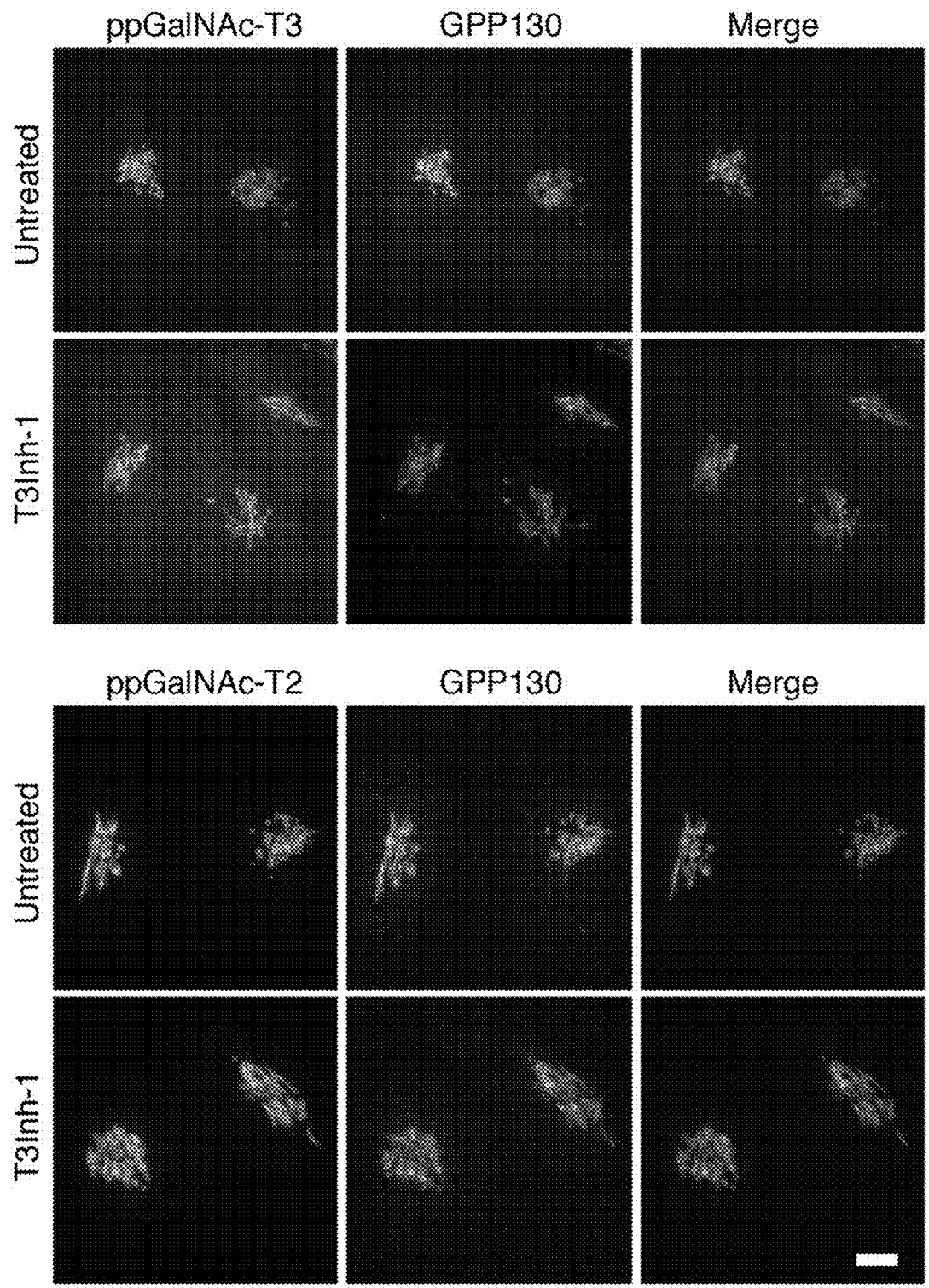
FIG. 4 shows that ppGalNAc-transferase levels are unaffected.
Figure 5A:
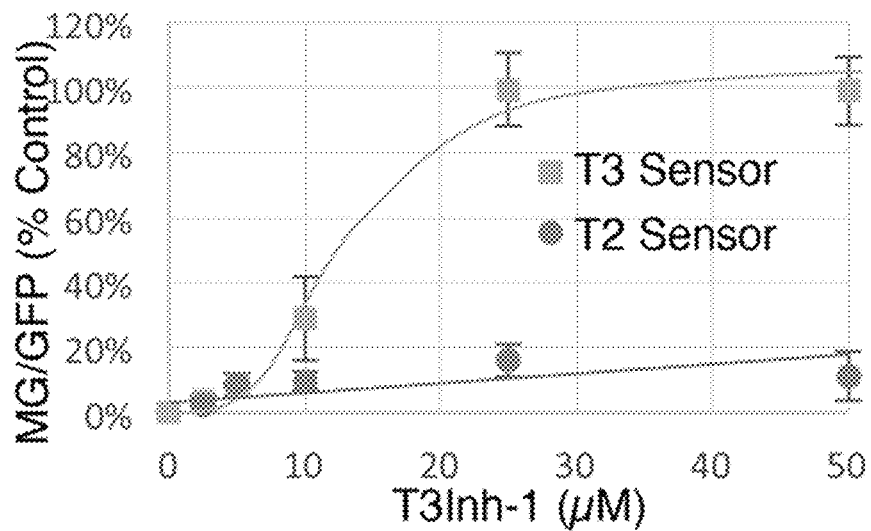
FIGS. 5A-5F show T3Inh-1 is a direct mixed-mode inhibitor of ppGalNAc-T3.
Figure 5B:
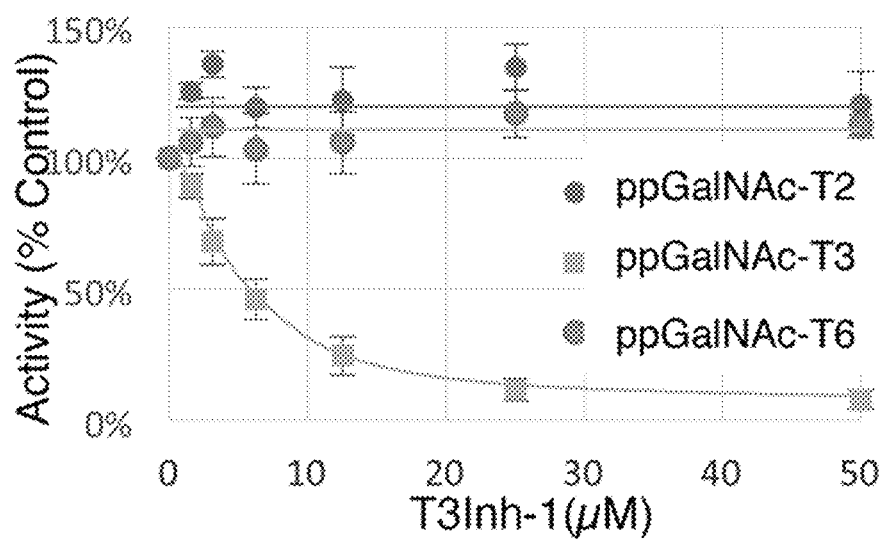
Figure 5C:
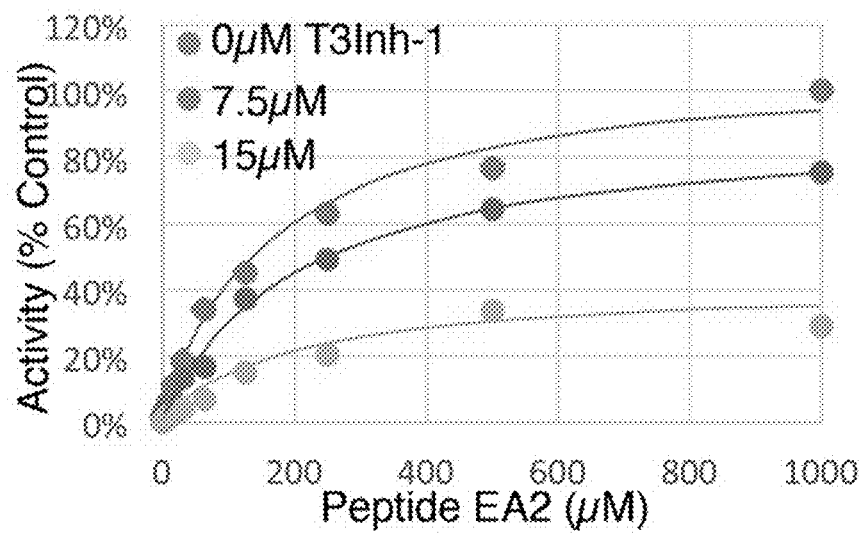
Figure 5D:
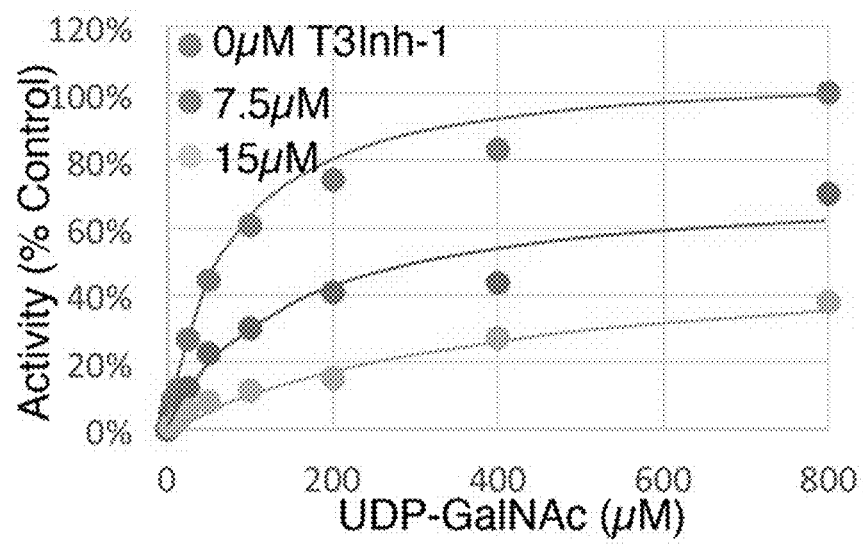
Figure 5E:
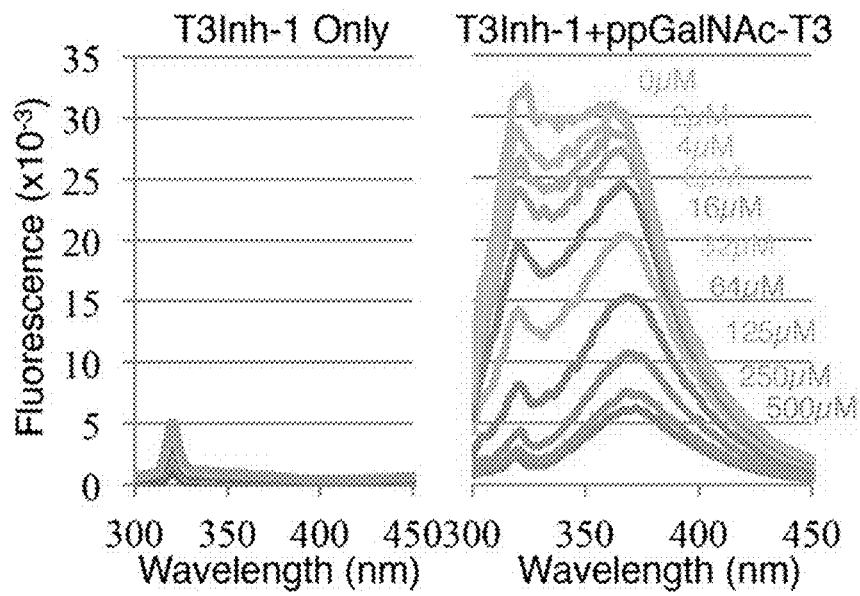
Figure 5F:
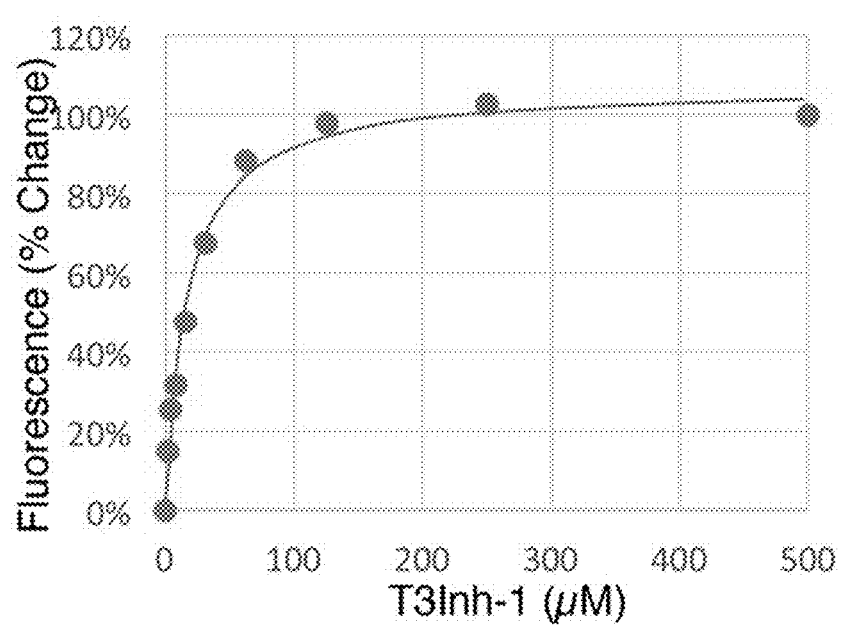
Figure 6A:
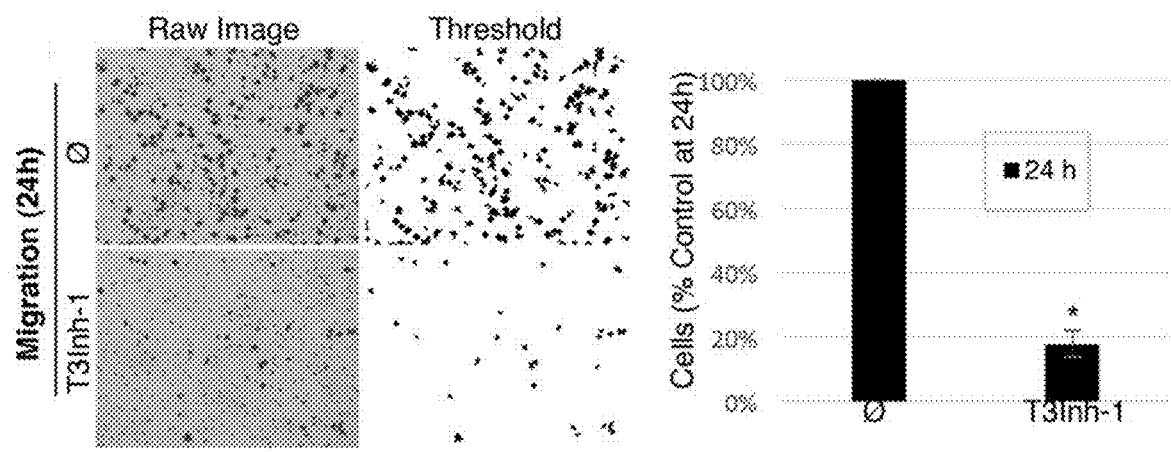
FIGS. 6A-6D show T3Inh-1 inhibits cell invasion.
Figure 6B:
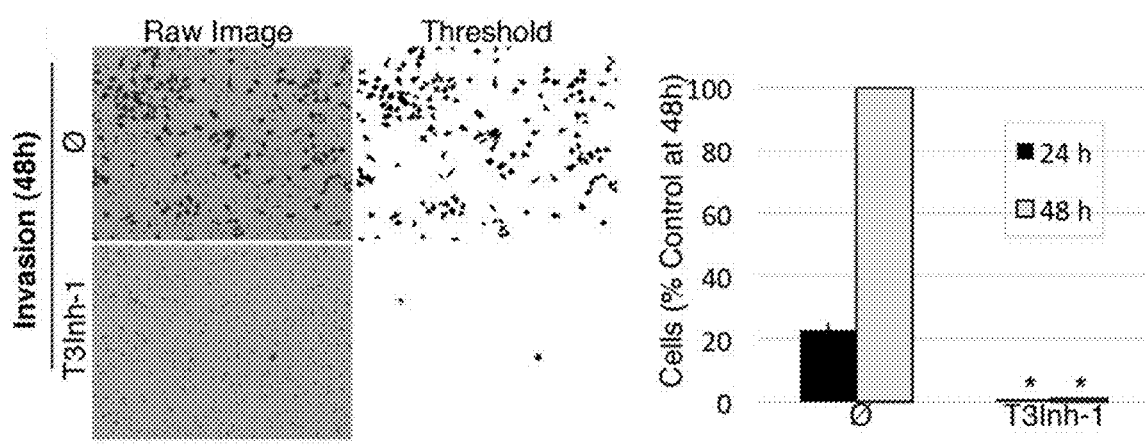
Figure 6C:
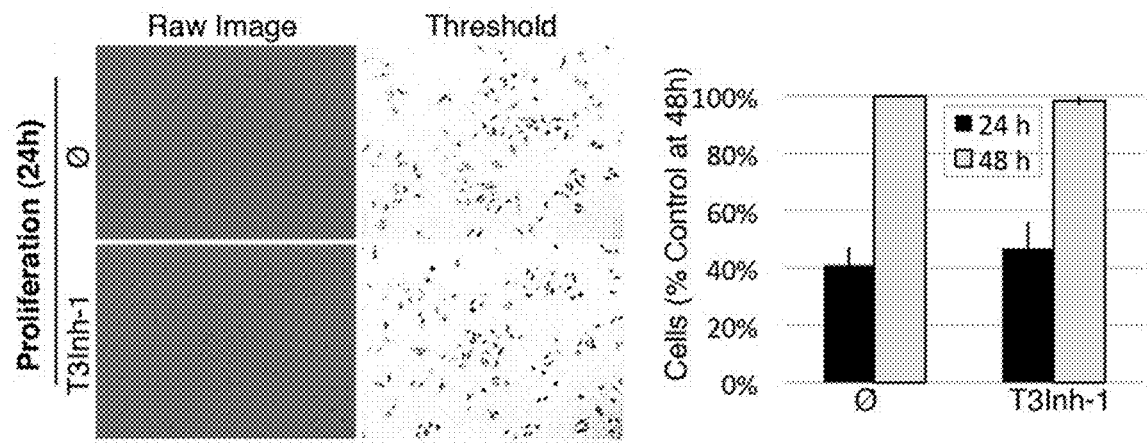
Figure 6D:
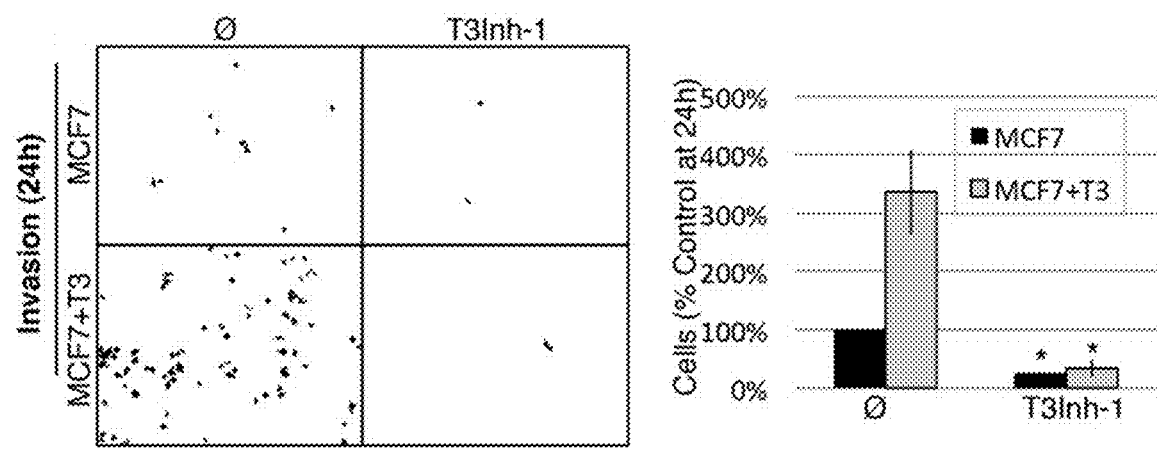

Importantly, T3Inh-1 exhibited no toxicity and did not affect HEK cell proliferation (FIG. 2). Also, a 24 h treatment did not affect staining intensity by the lectins Concanavalin A (ConA), Wheat germ agglutinin (WGA), Sambucus Nigra (SNA) or Vicia Villosa (VVA), which bind branched alpha-mannose, N-acetylglucosamine, sialic acid, or terminal GalNAc, respectively (FIG. 3). This implies that the enzymes contributing to the abundant glycans of N- and O-glycosylation detected by these lectins were unaffected and is consistent with ppGalNAc-T3 modifying a relatively limited number of substrates. Finally, there was no change in localization or expression level of ppGalNAc-T3, ppGalNAc-T2 or any other Golgi marker tested (FIG. 4).

To determine the effective concentration of T3Inh-1 in cells and in vitro, it was retested at various doses against the sensors and against the purified enzymes. T3Inh-1 activated the T3 sensor with an apparent IC50 of 12 μM and showed little or no activity towards the T2 sensor (FIG. 5 (A). Similarly, T3Inh-1 was a potent and selective direct inhibitor of ppGalNAc-T3 (FIG. 5 (B). Inhibition of ppGalNAc-T3 occurred with an IC50 of 7 μM and was undetectable against ppGalNAc-T2. T3Inh-1 also lacked activity against ppGalNAc-T6 (FIG. 5 (B), which is the isozyme considered most closely related to ppGalNAc-T3.

Towards characterizing the mechanism of inhibition we used the in vitro assay with purified ppGalNAc-T3 and individually varied both peptide and UDP-GalNAc substrate concentrations in the presence of 0, 7.5 or 15 μM T3Inh-1. The results were similar for both substrates (FIG. 5 (C and D), where T3Inh-1 decreased the Vmax and increased the Km (Table 1) indicating a mixed-mode of inhibition in which the inhibitor most likely binds both free enzyme to reduce substrate binding and enzyme-substrate complexes to reduce turnover. Implied in this model of action is direct binding to the enzyme typically at an allosteric site. To test for direct binding, intrinsic tryptophan fluorescence of ppGalNAc-T3 was determined in the presence of increasing T3Inh-1 concentrations. At all concentrations, the compound itself yielded miniscule signals, whereas the compound had a profound and dose-dependent effect on the ppGalNAc-T3 emission spectrum (FIG. 5 (E). These results confirmed direct binding with an apparent Kd of 17 μM (FIG. 5 (F). The similarity in concentration dependence of sensor activation in cells, in vitro inhibition and direct binding argues that T3Inh-1 acts directly on cellular ppGalNAc-T3 and inhibits its activity.

Table 1, below, provides the inhibition by T3Inh-1 at varying substrate concentrations. Values shown were determined from the data in FIG. 5 using Prism.

TABLE 1

| Substrate | Parameter | 0 μM | 7.5 μM | 15 μM |
|---|---|---|---|---|
| Peptide (EA2) | Vmax | 100% | 82% | 36% |
|  | Km (μM) | 173.7 | 208.4 | 210.3 |
|  | Ki (μM) |  | 9.9 |  |
| UDP-GalNAc | Vmax | 100% | 71% | 56% |
|  | Km (μM) | 74.9 | 153.4 | 448.3 |
|  | Ki (μM) |  | 2.9 |  |

Example 2

Figure 7A:
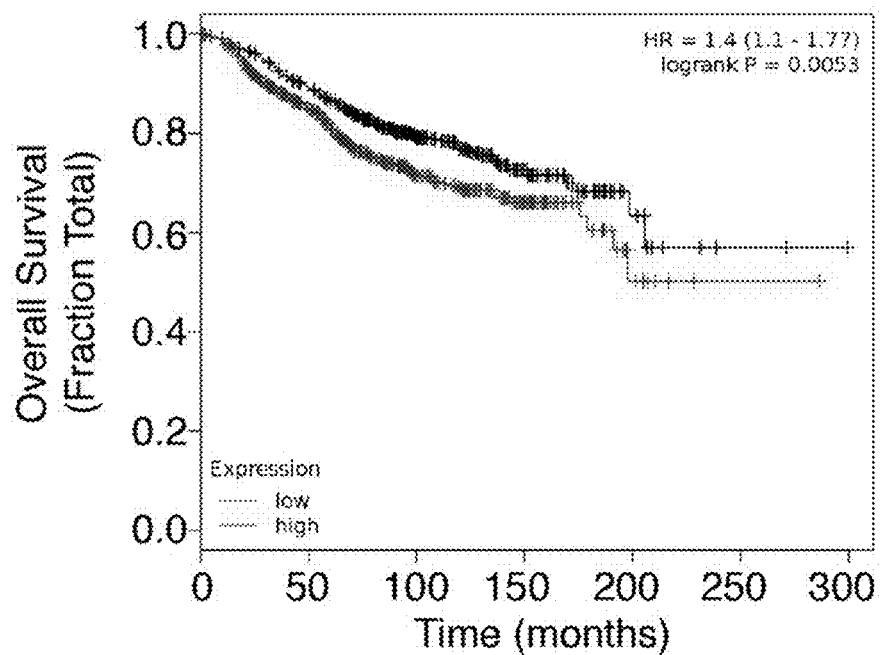
FIGS. 7A-7C illustrate breast cancer survival as a function of ppGalNAc-T3 expression and ppGalNAc-T3 expression in cultured breast cancer cell lines.
Figure 7B:
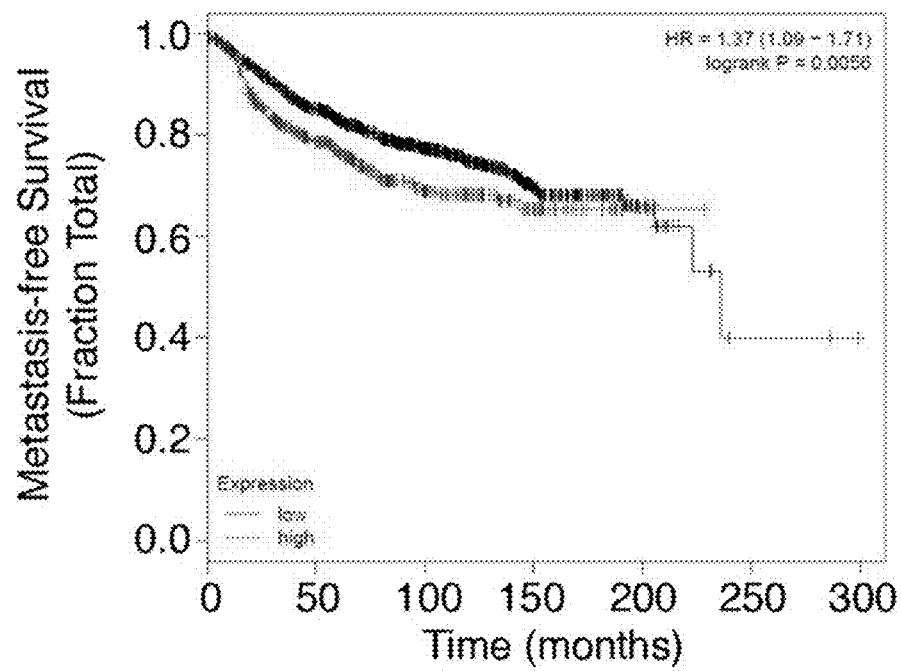
Figure 7C:
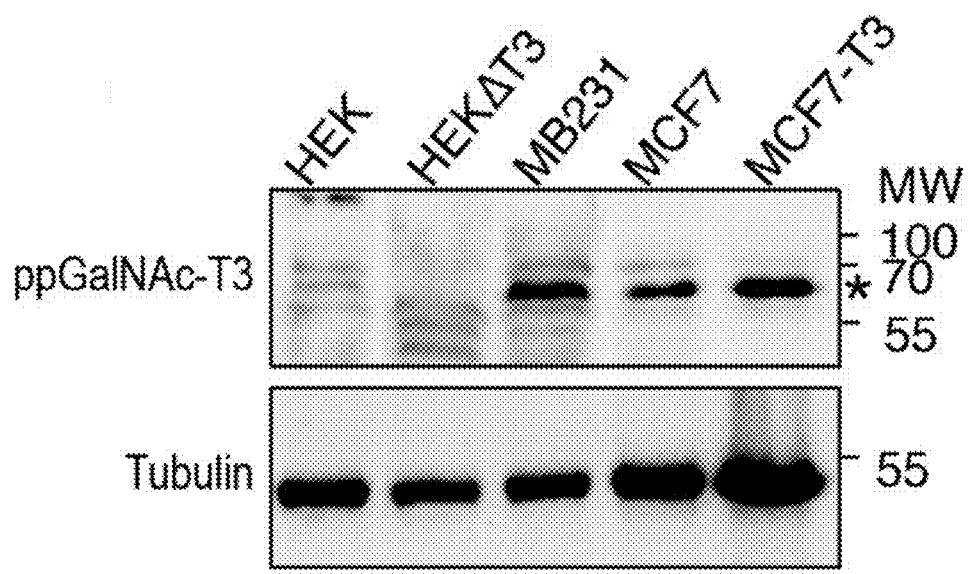

Given its validation as a direct inhibitor of ppGalNAc-T3 without obvious off-target effects we turned to biologically relevant tests of T3Inh-1. As mentioned, overexpression of ppGalNAc-T3 is linked to cancer cell invasiveness as well as poor outcomes in patients. Although no linkage to breast cancer has been reported, our analysis of publically available data for 1117 breast cancer patients using Kaplan-Meier survival plots shows that high expression of ppGalNAc-T3 correlates with poor patient overall and metastasis-free survival (FIG. 7 (A and B). Therefore, we carried out migration and invasion assays with the breast cancer cell line MDA-MB231, which expresses a relatively high level of ppGalNAc-T3 (FIG. 7 (C), in the absence or presence of 5 μM T3Inh-1. Cells were cultured on uncoated (to assay migration) or Matrigel-coated (to assay invasiveness) BIO-BOAT™ filters for 24 or 48 h and those cells that moved to the underside of the filters were imaged and quantified. T3Inh-1 was strikingly effective, inhibiting migration by >80% (FIG. 6 (A) and invasion by 98% (FIG. 6 (B) while causing no discernable effect on cell proliferation (FIG. 6 (C). To confirm that the effect was due to ppGalNAc-T3, the same experiment was carried out using MCF7 cells, which is a breast cancer cell line that expresses relatively low levels of ppGalNAc-T3 (FIG. 7 (C). Critically, invasion by MCF7 cells was significantly increased by transfection with ppGalNAc-T3 and this increase was strongly blocked by T3Inh-1 (FIG. 6 (D). Although O-glycosylation has been connected to cancer migration and invasion there is little evidence that it could be targetable for clinical purposes. Our results provide a "proof of concept" and a strong starting point for developing the necessary tools.

Example 3

Figure 8A:
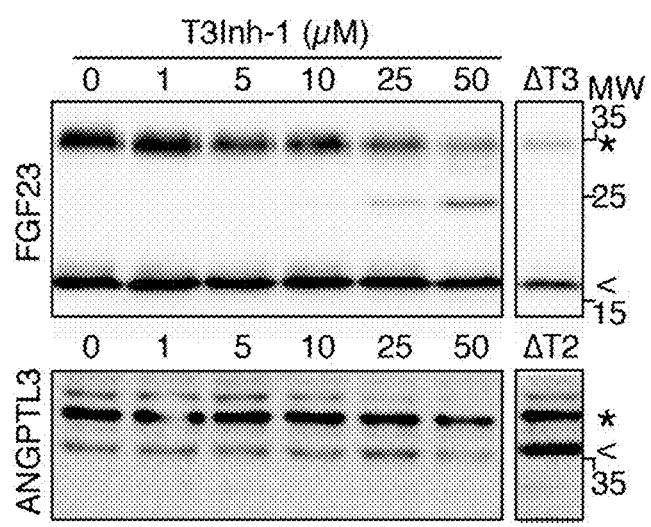
FIGS. 8A-8C show T3Inh-1 increases cleavage of FGF23.
Figure 8B:
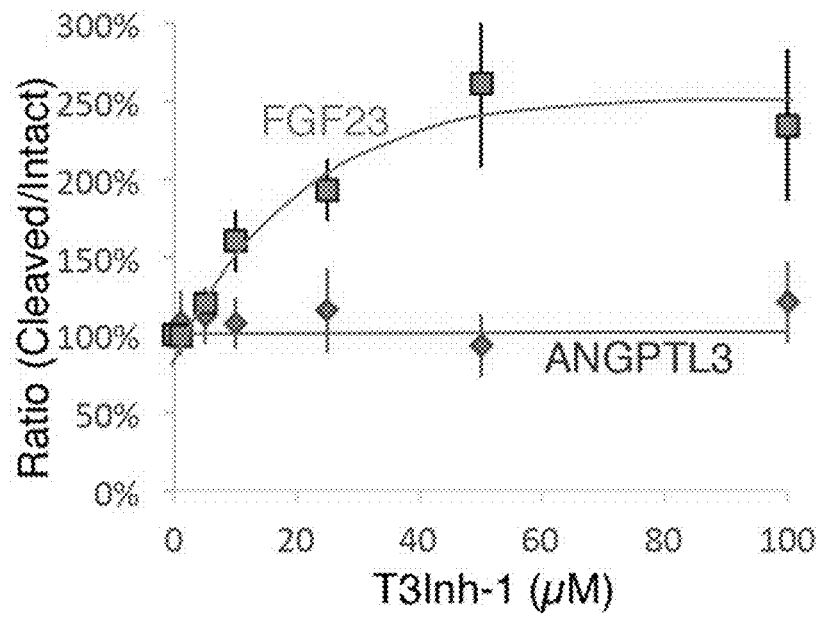
Figure 8C:
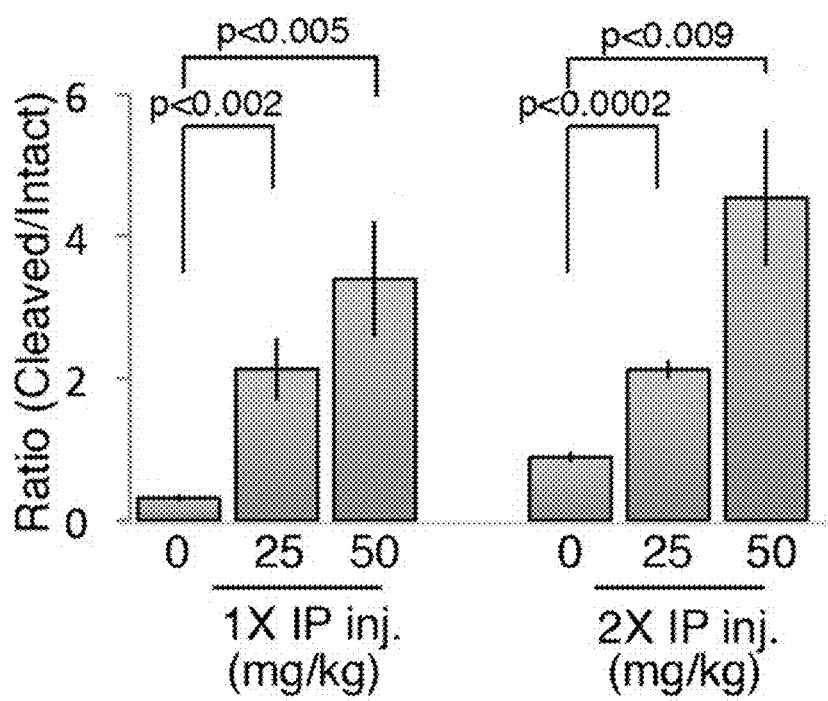
Figure 9A:
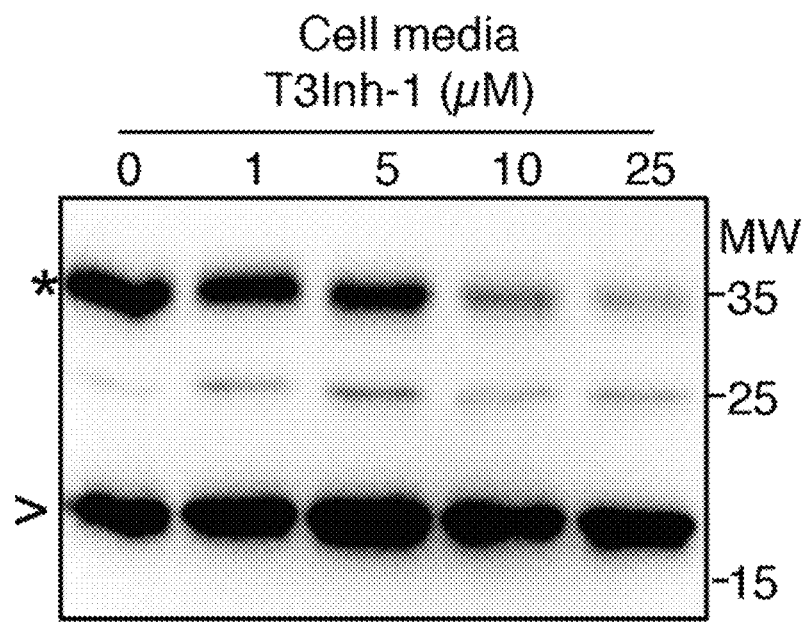
FIGS. 9A-9E secreted and cellular FGF23 after T3Inh-1 treatment.
Figure 9B:
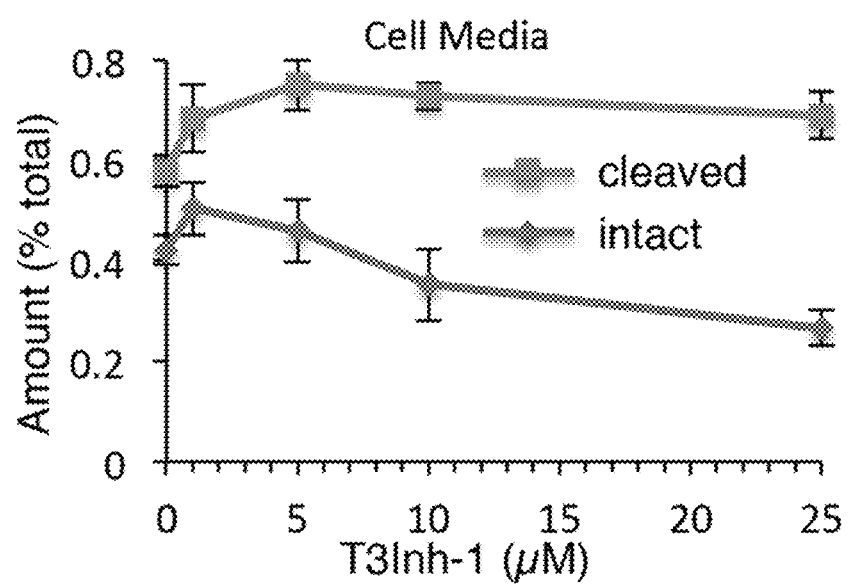
Figure 9C:
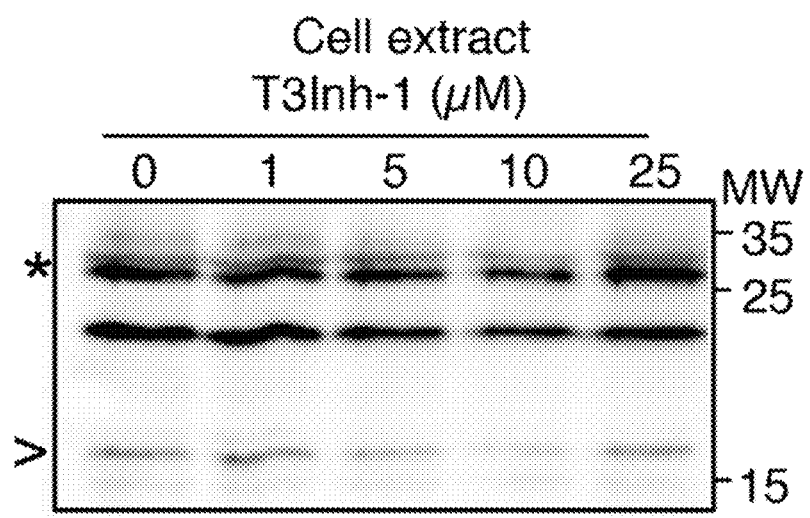
Figure 9D:
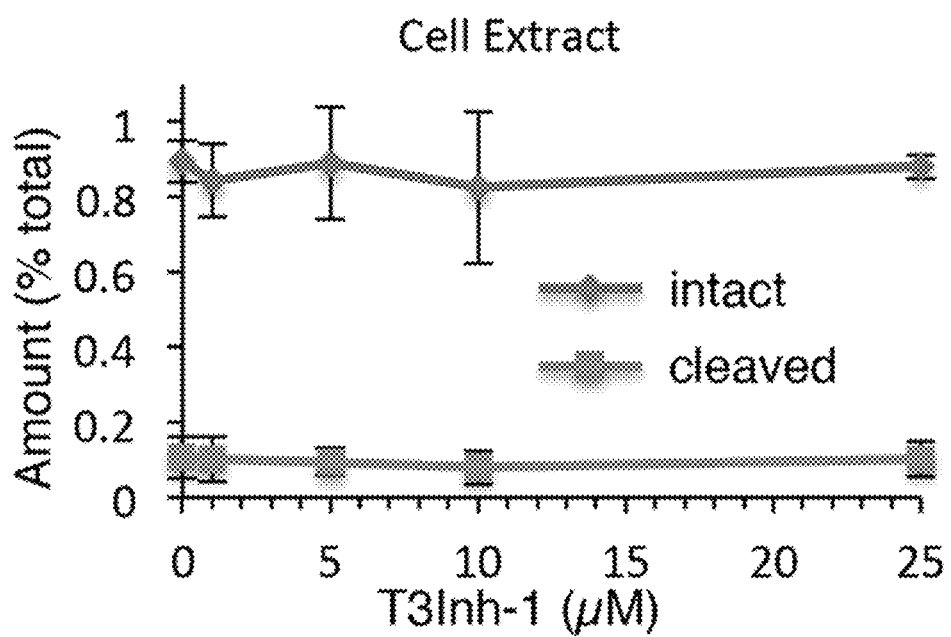
Figure 9E:
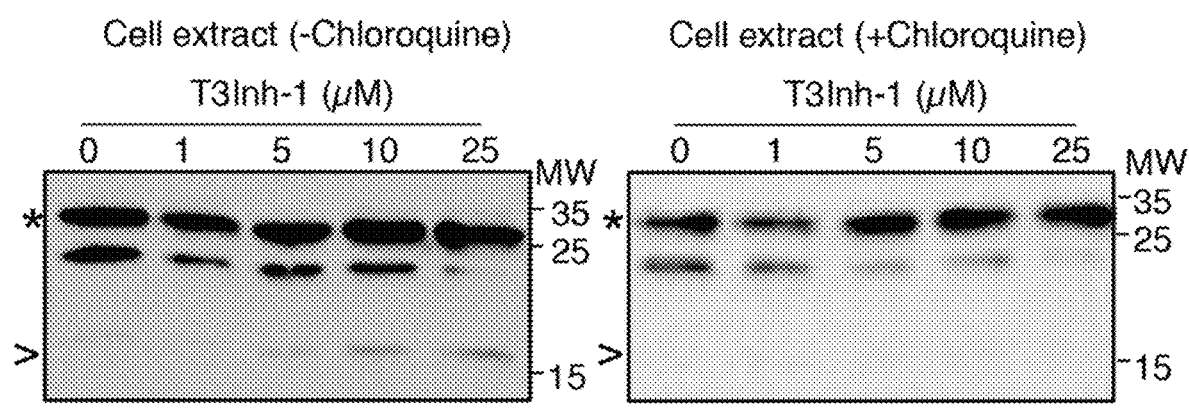

As the relevant target(s) of ppGalNAc-T3 that drive metastatic-like cell behavior remain to be identified, we next tested whether T3Inh-1 could inhibit glycan masking of FGF23, a known ppGalNAc-T3 target. If so, we expected reduced secretion of intact FGF23. HEK cells co-expressing transfected FGF23 and ppGalNAc-T3 were treated with increasing concentrations of T3Inh-1 and secreted FGF23 was assayed by immunoblot. There was a clear dose-dependent loss of intact FGF23 (FIG. 8 (A) and an increase in the ratio of cleaved/intact yielding a half-max of 14 μM for this effect (FIG. 8 (B). For an unknown reason, perhaps related to its instability in media, the cleaved fragment did not show a corresponding increase. Rather, its recovery varied with the average over three experiments yielding a relatively small increase (FIG. 9 (A and B). As expected, intact and cleaved FGF23 showed no change in cell lysates even for cells with lysosomal degradation inhibited by chloroquine FIG. 9 (C-E) arguing that T3Inh-1 affected cleavage just prior to secretion and did not affect FGF23 expression or cause intracellular routing to lysosomes. Importantly, we also tested the effect of T3Inh-1 on cleavage of ANGPTL3, which is controlled by ppGalNAc-T2-mediated glycan masking. Secreted intact ANGPTL3 remained high at all concentrations, confirming the selectivity of T3Inh-1 towards ppGalNAc-T3 FIG. 9 (A and B). Reasoning that we might be able to see a similar effect on secreted FGF23 in an animal model, mice were injected intraperitoneally with T3Inh-1 and serum levels of cleaved FGF23 were determined. Three groups (0, 25 and 50 mg/kg T3Inh-1) of mice received either one or two injections separated by 24 h, followed by blood collection after another 24 h. There were no apparent ill effects on animal health. An ELISA assay with antibodies against the N- and C-terminal portions of FGF23 was used to determine the ratio of cleaved/intact FGF23 in the blood. Remarkably, T3Inh-1 caused a robust and statistically significant increase in this ratio at the tested 25 and 50 mg/kg concentrations (FIG. 9 (C). These findings support the further development of T3Inh-1 toward mitigating the effects of elevated FGF23 signaling in chronic kidney disease patients.

CONCLUSION

We identified an isozyme-selective inhibitor targeting ppGalNAc-T3. The compound binds directly conferring a mixed-mode of inhibition and is equally active in vitro and in cells. Its discovery paves the way for structural studies that will contribute to our understanding of the enzyme reaction mechanism and guide rational design of modified versions of T3Inh-1 to improve its binding affinity and efficacy. Forthcoming tests of disease models, possibly employing higher affinity versions, may strengthen the case for therapeutic uses of T3Inh-1. It is difficult to predict possible side effects because a full list of ppGalNAc-T3 substrates is not yet available. However, the known effects of its knockout in the mouse model are all attributed to FGF23 processing. Thus, use of T3Inh-1 to reduce intact FGF23 (and increase the inhibitory cleaved fragment) to treat chronic kidney disease may have limited side effects. Clearly, the issue of multiple substrates has not been a major concern in successful therapies targeting protein kinases. To conclude, we anticipate rational design aided by T3Inh-1, as well as further screening using isozyme-specific sensors, to result in a panel of both isozyme- and pan-specific modulators targeting ppGalNAc-transferases. As individual ppGalNAc-transferase isozymes are associated with unique diseases, the result would be a new class of therapeutics capable of treating an array of differing diseases.

Materials and Methods:

Cell lines and antibodies. HEK cell lines were previously described. HeLa (Cat #ATCC-CCL-2, CVCL_0030), MDA-MB231 (Cat #ATCC-HTB-26, CVCL_0062), and MCF7 (Cat #ATCC-HTB-22, CVCL_0031) were purchased from ATCC (Manassas, Va.). All cell lines were verified mycoplasma free every two months using Hoechst staining. Antibodies used were monoclonal antibodies 4C4 against ppGalNAc-T2 and UH5 against ppGalNAc-T3, monoclonal 9e10 against the myc epitope, a polyclonal against the FLAG epitope (Bethyl Labs, Cat #A190-102B, AB_1944186), a polyclonal against GPP130, a purchased anti-ppGalNAc-T3 antibody (ThermoFisher, Cat #PA5-

25217, AB_2542717), an anti-α-tubulin antibody (Biolegend, Clone TU-01, Cat #625902, AB_2210041), Alexa 488 anti-mouse (Cat #A28175, AB_2536161) and Alexa 555 anti-rabbit (Cat #A27039, AB_2536100) from Thermo Fisher (Pittsburgh, Pa.), and horse radish peroxidase-conjugated goat anti-mouse (Cat #170-6516, AB_11125547) and goat anti-rabbit (Cat #170-6515, AB_11125142) antibodies from Sigma-Aldrich (St. Louis, Mo.).

Primary screen. HEK cells stably expressing the T2 sensor (containing ANGPTL3 linker sequence with T225G modification) or the T3 sensor (containing FGF23-based linker) were cultured in MEM (Corning, N.Y., Cat #10-010-CV) with 10% fetal bovine serum (FBS, Atlanta Biologicals, Flowery Branch, Ga., Cat #5111150) and 100 IU/ml penicillin-streptomycin (Sigma-Aldrich, Cat #P4333) at 37° C., 5% CO2. Positive controls were cell lines expressing matched sensors with the glycosylation site mutated (Δglycan), specifically T225G/T226G and T178G for the T2 and T3 sensors, respectively. Cells (50,000/well) were seeded in flat bottom 96-well-plates (Corning, N.Y., Cat #3997) and grown for 24 h. Compounds (the diversity set from ChemBridge Corporation (Chicago, Ill.) and the approved oncology drugs set V and the diversity set II from the National Cancer Institute Developmental Therapeutics Program) were then added to achieve a 10 µM final concentration. After 6 h, the medium was aspirated and the cells were released by adding 100 µl 5 mM EDTA/PBS containing 110 nM MG dye (Sharp Edge Labs, Pittsburgh, Pa.) for 5 min at 37° C. The plates were then transferred to an Accuri™ C6 flow cytometer (BD Biosciences) where GFP and MG fluorescence was measured using 488 nm and 640 nm for 10,000 cells per well. Data analysis used FlowJo software (www.flowjo.com, SCR_008520). For each well the geometric means of the MG and GFP signals were used to compute the MG/GFP ratio. Each compound was analyzed in two wells and the average of the two resulting ratios (R) was recorded. Each daily run included at least 16 wells of vehicle-only controls (sensor-expressing cells treated with a matching DMSO concentration (Fisher Scientific, Cat #BP231-100)) and a similar analysis was used to calculate their average MG/GFP ratio (RNeg) and its standard deviation (SDNeg). The Q value of each compound (as well as the untreated Δglycan positive controls) was calculated by using the following equation: Q=(R−RNeg)/SDNeg. Background fell within the range −2.5≤Q≤3 and the average QΔglycan was 135 and 38 for the T2 and T3 sensors, respectively.

Secondary screen. Glycosylation assays using recombinant ppGalNAc-T2 and ppGalNAc-T3 were carried out using the UDP-GLO™ Glycosyltransferase assay kit (Promega, Madison, Wis., Cat #V6962), according to the manufacturer's recommendation. The reaction (25 µl) included 2.5 ng/µl purified enzyme, 25 µM UDP-GalNAc (Sigma-Aldrich, Cat #U5252), 12.5 µM EA2 peptide (AnaSpec, Mucin 10, AA153-165, PTTDSTTPAPTTK, Cat #AS-63841), 25 mM Tris-HCl (pH7.5) (Fisher Scientific, Cat #77-86-1), 5 mM MnCl2 (Fisher Scientific, Cat #M87-500), 2.5 mM CaCl2 (Fisher Scientific, Cat #C70-500) and 50 µM compound. The negative control was vehicle only (same reaction mixture with a matched percentage of DMSO instead of compound), whereas background was from the reaction carried out without enzyme and DMSO instead of compound. All reactions were incubated at 37° C. in a water bath for 30 min and then cooled to room temperature. Aliquots (5 µl) were then added to 384-well plate (Thermo Scientific, Waltham, Mass., Cat #164610) to which 5 µl of UDP Detection Reagent was also added. Duplicate measures were made for all reactions. After 1 h at room temperature the luminescent signals were determined using a Tecan Infinite M1000 (Tecan Group Ltd., Männedorf, Switzerland) with integration time set to 1000 msec. The background-subtracted average for each compound was expressed as a percentage of the negative control (taken as 100%). Compounds with ≥50% effect were considered direct modulators.

Titration assays. For the sensor assay, about 200,000 cells expressing either sensor were seeded into Greiner Bio-One 24-well plates (Sigma-Aldrich, Cat #662160). After 24 h, the cells were incubated for another 6 h in the presence of 0-50 µM compound. To release the cells the medium was replaced with 200 µl 5 mM EDTA/PBS containing 110 nM MG dye. After 5 min at 37° C., fluorescence measurements (20,000 cells/well) were carried out as described above. For the biochemical assay, the assay conditions were identical except for variations in the compound or substrate concentrations as indicated in the figure legends. Data analysis was completed using Prism (Graph Pad Prism Inc., SCR_002798).

Tryptophan fluorescence quenching assay. The purified lumenal domain of ppGalNAc-T3 (30 ng/µl) was incubated with 0-500 µM compound at room temperature for 10 min and 200 µl aliquots were transferred to a Greiner Bio-One 96-well glass-bottom plate (Sigma-Aldrich, Cat #655892) and the fluorescent emission was scanned (300-450 nm) using a Tecan Infinite M1000 with excitation at 290 nm, gain set to 150, number of flashes at 50 and flash frequency at 400 Hz. The value at the peak of emission at 324 nm was used for the binding curve analysis by Prism.

Microscopy. For determination of sensor activation, spinning-disk confocal microscopy was used exactly as described. To assess possible effects of compounds on Golgi markers, including ppGalNAc-T2 and ppGalNAc-T3, immunofluorescence was carried on HeLa cells treated with 10 µM compound for 6 h. Briefly, the cells were grown on 12 mm diameter coverslips (Fisher Scientific, Cat #12-545-81) for 48 h, treated with the compounds, washed with PBS and fixed with 3% paraformaldehyde (Sigma-Aldrich, Cat #P6148) for 15 min. Blocking, Triton X-100 permeabilization, antibody incubations and image capture by spinning-disk confocal were as described. Monoclonal antibodies against ppGalNAc-T2 and T3 were used undiluted and the polyclonal against GPP130 was used at 1:2000. All corresponding images were acquired and adjusted using identical parameters.

Lectin staining. HeLa cells (treated with T3Inh-1 for 24 h at the indicated concentrations) were washed twice in PBS containing 0.5% FBS then stained for 30 min with fluorescent lectins ConA (Cat #FL-1001), WGA (Cat #FL-1021), SNA (Cat #FL-1301) or VVA (Cat #FL-1231) (Vector Laboratories, Burlingame, Calif.) at 1:100 dilutions (except WGA used at 1:1000) in the wash buffer. After staining, the cells were washed twice, lysed with 0.2% Triton X-100 (Fisher Scientific, Cat #BP151-100) for 15 min at 4° C., centrifuged at 14,000×g for 15 min at 4° C., and the supernatants were read in a Greiner Bio-One 96-well glass-bottom plate using a Tecan Infinite M1000 with excitation at 495 nm and emission from 510-550 nm. Three independent trials were carried out and the peak value (520 nm) was used for quantification.

Proliferation assay. Equal numbers of HEK or MDA-MB231 cells were plated in Greiner Bio-One 24-well dishes in growth medium containing 0-50 µM T3Inh-1. After 24, 48 or 72 h, the cells were released using trypsin and counted twice using a hemocytometer for 3 independent trials.

Cell invasion assay. Breast cancer MDA-MB231 cells were grown in DMEM medium (Corning, N.Y., Cat #10-

013-CV) with 10% FBS and 100 IU/ml penicillin-streptomycin at 37° C. and 5% CO2 and then plated at a density of 1.32×104 in 0.3 ml of DMEM medium without FBS into the upper chamber of a BIOBOAT™ insert fitted with a 8.0 μm PET membrane (Corning, N.Y., Cat #354578). For migration assays, the filter was uncoated. For invasion assays, it was pre-coated with 100 μl MATRIGEL™ (BD Biosciences, Cat #356234) at concentration of 272 μg/ml for 1-2 hours at room temperature. Medium containing 10% FBS (0.6 ml) was placed into the lower chamber as a chemo attractant. The compound (final concentration of 5 μM) or a matching amount of DMSO was added to both chambers. After 24 h or 48 h the cells were fixed with −20° C. methanol for 15 min and then stained with Trypan blue for 5 min. Cells on the upper surface were removed using cotton swabs. Cells present on the underside of the membrane were photographed using an EVOS FL Cell Imaging System (Invitrogen, CA) and the images were thresholded for presentation and counting using Image J (National Institutes of Health, Bethesda, Md., SCR_003070). The assays involving MCF7 cells were identical except that they were performed 24 h post transfection.

Immunoblotting. The FLAG-tagged FGF23, Myc-tagged ANGPTL3 with the T225G modification, and untagged ppGalNAc-T3 (cloned into PCDNA 3.0 using BamH1 sites) were transfected into HEK cells using the JetPEI transfection reagent (VWR International, Radnor, Pa., Cat #101-40N) according to the manufacturer's instructions. After 24 h, the medium was replaced with serum-free MEM containing the compound for 6 h. The medium and cells were then collected and, after trichloroacetic acid precipitation of the medium, analyzed by immunoblot using anti-FLAG antibody at 1:1000 or anti-Myc antibody at 1:2000 and then the peroxidase-coupled secondary antibodies. Emission was captured and quantified using a CHEMIDOC™ Touch Imaging System with Image Lab Software (BioRad, SCR_014210). For ppGalNAc-T3 determinations in different cell lines, cells were collected and lysed with 100 μl buffer (10 mM Tris-HCl (pH8.0), 1 mM EDTA (ACROS ORGANICS, Cat #446085000), 1% Triton X-100, 0.1% sodium deoxycholate (Fisher Scientific, Cat #BP349-100), 0.1% SDS (Fisher Scientific, Cat #BP166-500), 140 mM NaCl (Fisher Scientific, Cat #5271-3), 1 mM PMSF (Sigma-Aldrich, Cat #PMSF-RO). Then 15 μl of each lysate was analyzed by immunoblotting using the purchased anti-ppGalNAc-T3 and anti-α-tubulin antibodies.

Animal analysis. Wild-type C57BL/6 six to eight week old mice were purchased from Charles River Laboratories International Inc. (Wilmington, Mass.). Protocols, handling, and care of the mice conformed to protocols approved by the Institutional Animal Care and Use Committee of Carnegie Mellon University (CMU IACUC protocol AS16-005). The compound was dissolved in DMSO at 25 and 50 mg/ml then further diluted with PEG400 (Hampton Research, CA, USA, HR2-603) to create 5 and 10 mg/ml stocks for injection. Control (vehicle only: 20% DMSO, 80% PEG400) and experimental (25 or 50 mg/kg compound) animals received either single or double (separated by 24 h) intraperitoneal injections and, 24 h after the last injection, a cardiac blood draw was carried out. The cleaved/intact FGF23 ratio was determined using ELISA kits from Immunotopics (Carlsbad, Va., USA, Cat #60-6800, Cat #60-6300) with cleaved equaling total minus intact.

Example 4

A ppGalNAc-T1 biosensor was prepared and expressed essentially as described above for the ppGalNAc-T2 and T3 biosensors. Nucleic acid and protein sequences of the ppGalNAc-T1 biosensor are provided in FIG. 10. Other than the furin/gly sequence the consensus sequences are the same as described above with respect to T2/T3.

Figure 13A:
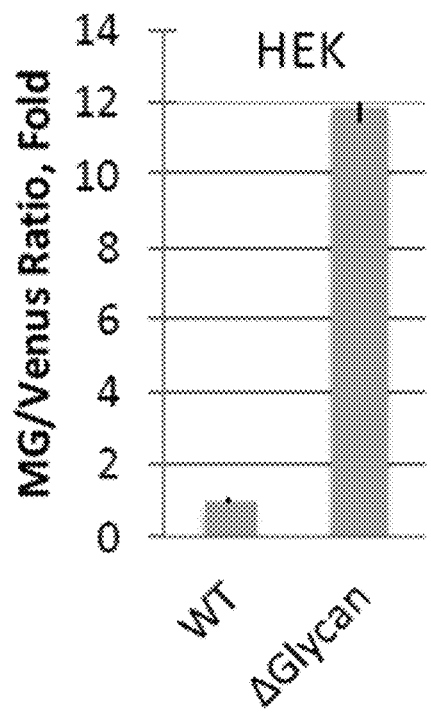
FIGS. 13A-13C show testing of the T1 sensor.
Figure 13B:
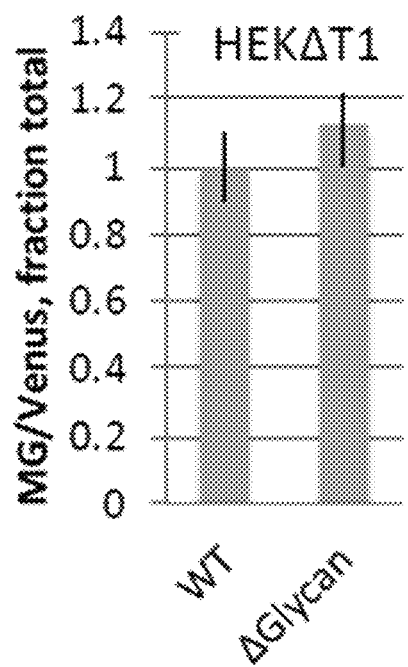
Figure 13C:
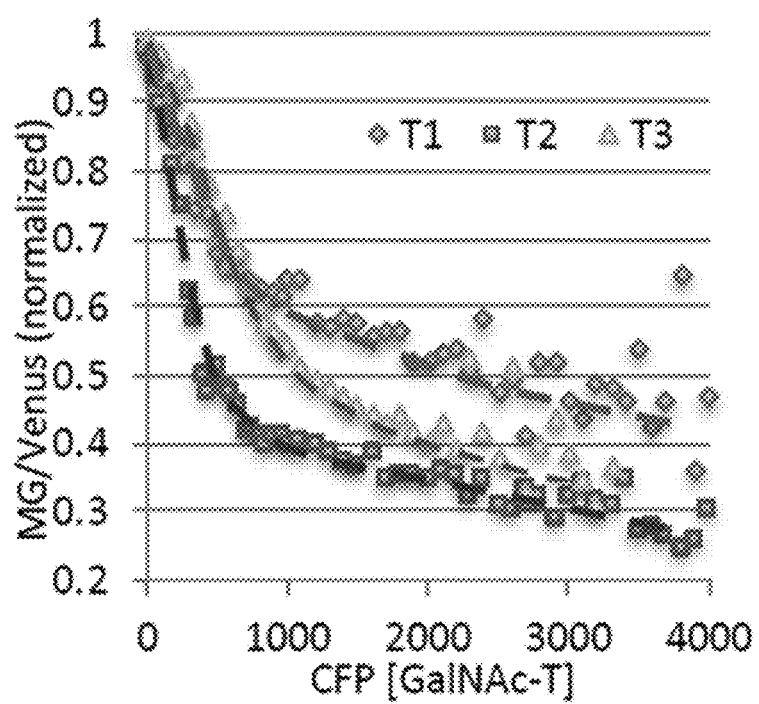

We initially chose T1 target sequences DETVTASTQAD from osteopontin and LSGVTASTGA from bone sialoprotein and these were used to generate the starting sequence EFVTRSYR, which incorporates a furin recognition sequence. Upon testing, this was not cleaved well so the furin site was separated from the "consensus" site for glycosylation. The sequence was further refined to add an acidic residue and a proline, and the sequence REDRATPSYDD yielded low background and was strongly activated by mutation of the acceptor threonine to glycine. But, the isozyme selectivity test showed a further need for refinement so new versions were constructed including REDRVTGSYQ reinserting the consensus valine and removing the proline (because it is a residue preferred by many GalNAc-T isozymes). This proved successful. The resulting T1 sensor showed 12-fold activation (220 SD) using Δglycan in HEK (FIG. 13 (A) and it was fully activated in ΔT1 cells (FIG. 13 (B). The dose dependence test was next using transfection of CFP-T1 into ΔT1 cells expressing the new T1 sensor. As we had not previously performed this test, it was simultaneously carried out for the T2 and T3 sensors. The result was striking (FIG. 13 (C). For each sensor, including the new T1 sensor, expression of the corresponding enzyme yielded a clear, dose-dependent decrease in its activation level. Activation in cells deleted for the respective enzymes shows the isozyme selectivity of each sensor and dose-dependent loss of this activation upon re-introduction of the missing GalNAc-T shows the activity-relationship. GalNAc-T1 is clearly biologically and medically relevant. The ability to assay its activity in situ is a significant step and allows us to initiate screening for inhibitors of T1 that will also be powerful reagents for research and therapeutic purposes.

The following numbered clauses are illustrative of various aspects of the invention.

Clause 1: A method for treating chronic kidney disease in a patient, comprising, inhibiting O-glycosylation by administering to a patient in need thereof an amount of a GalNAc transferase-3 inhibitor effective to treat chronic kidney disease in a patient.

Clause 2: The method of clause 1, wherein the GalNAc transferase-3 inhibitor lowers endocrine hormone fibroblast growth factor-23 activity in the patient, thereby regulating phosphate homeostasis and improving chronic kidney disease in the patient.

Clause 3: The method of clause 2, wherein the GalNAc transferase-3 inhibitor lowers endocrine hormone fibroblast growth factor-23 activity in the patient by promoting cleavage of endocrine hormone fibroblast growth factor-23 by furin.

Clause 4: A method for inhibiting cancer metastasis in a patient, comprising, inhibiting O-glycosylation by administering to a patient in need thereof an amount of a GalNAc transferase-3 inhibitor effective to reduce invasiveness of cancer thereby inhibiting cancer metastasis in a patient.

Clause 5: The method of clause 4, wherein the GalNAc transferase-3 inhibitor inhibits O-glycosylation, thereby decreasing cancer cell invasiveness in the patient.

Clause 6: The method of clause 4 or clause 5, wherein the cancer is breast cancer.

Clause 7: The method of any one of clauses 1-6, wherein the GalNAc transferase-3 inhibitor has the following structure:

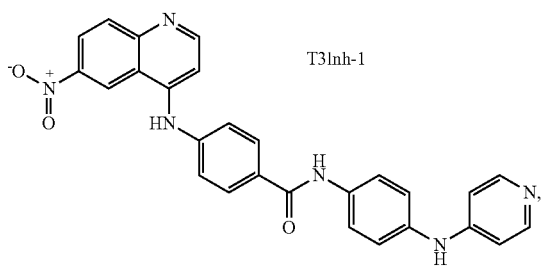

or a pharmaceutically-acceptable salt thereof.

Clause 8: The method of any one of clauses 1-7, wherein the GalNAc transferase-3 inhibitor is a non-competitive/mixed-mode inhibitor of GalNAc transferase-3.

Clause 9: The method of any one of clauses 1-7, wherein the GalNAc transferase-3 inhibitor is administered to the patient in a unit dose or multiple doses ranging from 0.01 to 50 mg/kg, or from 10 to 25 mg/kg of weight of the patient.

Clause 10: A method for identifying a compound that inhibits GalNAc transferase-1 comprising:

a.) expressing in cells a sensor comprising a polypeptide comprising, in order, an FAP blocking domain having an FAP sequence of SEQ ID NOS: 5-11, a furin cleavage linker having the sequence REDRVTGSYQ (SEQ ID NO: 2), an FAP domain of SEQ ID NOS: 5-11, a transmembrane domain, and, optionally, a fluorescent protein domain;

b.) contacting the cells with a compound to be tested for GalNAc transferase 1 inhibitory activity, and an activatable malachite green fluorochrome, and c.) determining if ppGalNAc transferase-1 activity is inhibited based upon the presence or absence of fluorescence of an activatable malachite green compound that fluoresces when bound to the FAP domain of the sensor.

Clause 11: The method of clause 10, wherein when GalNAc transferase-1 activity is inhibited, glycosylation of a GalNAc transferase-1 isozyme-specific target site in the furin cleavage linker is prevented, and the blocking domain is released by cleavage of the sensor in the cell at the furin cleavage site of the furin cleavage linker, allowing for binding and activation of the activatable malachite green compound by the FAP domain, such that the bound activatable malachite green compound fluoresces when exposed to light at an excitatory wavelength for the bound activatable malachite green compound.

Clause 12: The method of clause 10, wherein the activatable malachite green compound is MG11p.

Clause 13: The method of clause 10, wherein the blocking domain and/or the FAP, independently have the sequence of amino acids 61-186 and 216-332, respectively of the amino acid sequence of SEQ ID NO: 4.

Clause 14: The method of clause 10, wherein the blocking domain has the sequence of amino acids 61-186 of the amino acid sequence of SEQ ID NO: 4, the FAP domain has the sequence of amino acids 216-332 of the amino acid sequence of SEQ ID NO: 4, the transmembrane domain has the sequence of amino acids 373-399 of the amino acid sequence of SEQ ID NO: 4, and the sensor comprises after the transmembrane domain, a fluorescent protein domain having the sequence of amino acids 404-640 of the amino acid sequence of SEQ ID NO: 4.

Clause 15: The method of clause 10, wherein the sensor has the amino acid sequence of SEQ ID NO: 4.

Clause 16: A fluorescent sensor of GalNAc-type O-glycosylation by GalNAc-T1 isozyme comprising, in order, an FAP blocking domain having a sequence of an FAP of SEQ ID NOS: 5-11, a furin cleavage linker having the sequence REDRVTGSYQ (SEQ ID NO: 2), an FAP domain of any one of SEQ ID NOS: 5-11, a transmembrane domain, and, optionally, a fluorescent protein domain.

Clause 17: The fluorescent sensor of clause 16, comprising a fluorescent protein domain after the transmembrane domain.

Clause 18: The fluorescent sensor of clause 16, wherein the blocking domain and/or the FAP, independently have the sequence of amino acids 61-186 and 216-332, respectively of SEQ ID NO: 4.

Clause 19: The fluorescent sensor of clause 16, wherein the blocking domain has the sequence of amino acids 61-186 of the amino acid sequence of SEQ ID NO: 4, the FAP domain has the sequence of amino acids 216-332 of the amino acid sequence of SEQ ID NO: 4, the transmembrane domain has the sequence of amino acids 373-399 of the amino acid sequence of SEQ ID NO: 4, and the sensor comprises after the transmembrane domain, a fluorescent protein domain having the sequence of amino acids 404-640 of the amino acid sequence of SEQ ID NO: 4.

Clause 20: The fluorescent sensor of clause 16, wherein the sensor has the amino acid sequence of SEQ ID NO: 4.

Clause 21: A nucleic acid comprising a gene for expression of a fluorescent sensor polypeptide of GalNAc-type O-glycosylation by a GalNAc-T1, isozyme, comprising an open reading frame encoding a polypeptide of any one of clauses 16-20.

Clause 22: A method of inhibiting O-glycosylation in a patient, comprising administering to the patient an amount of a GalNAc transferase-3 inhibitor has the following structure:

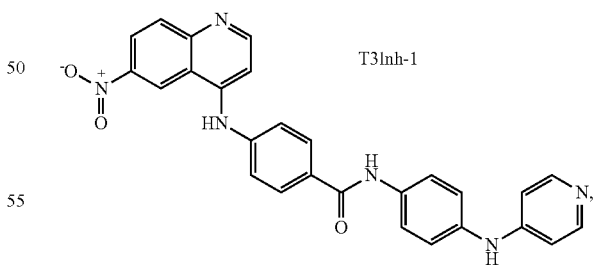

or a pharmaceutically-acceptable salt thereof effective to inhibit GalNAc transferase-3 in a patient.

Having described this invention, it will be understood to those of ordinary skill in the art that the same can be performed within a wide and equivalent range of conditions, formulations and other parameters without affecting the scope of the invention or any embodiment thereof.

The invention claimed is:

1. A fluorescent sensor of GalNAc-type O-glycosylation by GalNAc-T1 isozyme comprising a polypeptide comprising, in order, a fluorogen-activating protein (FAP) blocking domain having a sequence of an FAP of SEQ ID NOS: 5-11, a furin cleavage linker having the sequence REDRVTGSYQ (SEQ ID NO: 2), an FAP domain of any one of SEQ ID NOS: 5-11, a transmembrane domain, and, optionally, a fluorescent protein domain.

2. The fluorescent sensor of claim 1, further comprising a fluorescent protein domain after the transmembrane domain.

3. The fluorescent sensor of claim 1, wherein the blocking domain and/or the FAP independently have the sequence of amino acids 61-186 and 216-332, respectively, of SEQ ID NO: 4, or wherein the blocking domain has the sequence of amino acids 61-186 of the amino acid sequence of SEQ ID NO: 4, the FAP domain has the sequence of amino acids 216-332 of the amino acid sequence of SEQ ID NO: 4, the transmembrane domain has the sequence of amino acids 373-399 of the amino acid sequence of SEQ ID NO: 4, and the sensor comprises after the transmembrane domain, a fluorescent protein domain having the sequence of amino acids 404-640 of the amino acid sequence of SEQ ID NO: 4.

4. The fluorescent sensor of claim 1, wherein the sensor has the amino acid sequence of SEQ ID NO: 4.

5. A method for identifying a compound that inhibits GalNAc transferase-1 comprising:
   expressing the fluorescent sensor of claim 1 in cells;
   contacting the cells with a compound to be tested for GalNAc transferase-1 inhibitory activity and an activatable malachite green fluorochrome that fluoresces when bound to the FAP domain of the sensor; and
   determining if ppGalNAc transferase-1 activity is inhibited based upon the presence or absence of fluorescence of the activatable malachite green compound.

6. The method of claim 5, wherein when GalNAc transferase-1 activity is inhibited, glycosylation of a GalNAc transferase-1 isozyme-specific target site in the furin cleavage linker is prevented, and the blocking domain is released by cleavage of the sensor in the cell at the furin cleavage site of the furin cleavage linker, allowing for binding and activation of the activatable malachite green compound by the FAP domain, such that the bound activatable malachite green compound fluoresces when exposed to light at an excitatory wavelength for the bound activatable malachite green compound.

7. The method of claim 5, wherein the activatable malachite green compound is MG11p.

8. The method of claim 5, wherein:
   the blocking domain and/or the FAP independently have the sequence of amino acids 61-186 and 216-332, respectively, of the amino acid sequence of SEQ ID NO: 4; or
   the blocking domain has the sequence of amino acids 61-186 of the amino acid sequence of SEQ ID NO: 4, the FAP domain has the sequence of amino acids 216-332 of the amino acid sequence of SEQ ID NO: 4, the transmembrane domain has the sequence of amino acids 373-399 of the amino acid sequence of SEQ ID NO: 4, and the sensor comprises after the transmembrane domain, a fluorescent protein domain having the sequence of amino acids 404-640 of the amino acid sequence of SEQ ID NO: 4.

9. The method of claim 5, wherein the sensor has the amino acid sequence of SEQ ID NO: 4.

* * * * *

SEQUENCE LISTING

<160> NUMBER OF SEQ ID NOS: 18

<210> SEQ ID NO 1
<211> LENGTH: 1923
<212> TYPE: DNA
<213> ORGANISM: Homo sapiens

<400> SEQUENCE: 1

| | | | | | | |
|---|---|---|---|---|---|---|
| atggagacag | acacactcct | gctatgggta | ctgctgctct | gggttccagg | ttccactggt | 60 |
| gactatccat | atgatgtgcc | agattatgct | ggggcccagc | cggcctaccc | atacgacgtt | 120 |
| ccagactacg | ctctgcaggc | tagtggtggt | ggtggttctg | gtggtggtgg | ttctgctagc | 180 |
| caggtgcagc | tggtggagtc | tgagggaggc | ttggtacagc | ctggagggtc | cctgagactc | 240 |
| tcctgtgcag | cctctggatt | caccttcagt | agttatgaaa | tgaactgggt | ccgccaggct | 300 |
| ccaggtaagg | ggctggagtg | ggtctcacgt | attgatggtg | atgggagcag | cacaaactac | 360 |
| gcggactccg | tgaagggccg | attcaccatc | tccagagaca | acgccaagag | cacgctgtat | 420 |
| ctgcaaatga | atagtctgag | agccgaggac | acggctgtgt | attactgtac | aagggccaga | 480 |
| tactttggtt | cggtgagccc | ctacggtatg | gacgtctggg | gccaagggac | cacggtcacc | 540 |
| gtctcctcag | gaattctagg | atcgaactcg | agagaggaca | gagtcaccgg | tagctaccag | 600 |
| ggtggcggtg | gcagcggcgg | tggtggttcc | ggaggcggcg | gttctcaggc | tgtggtgact | 660 |
| caggagccgt | cagtgactgt | gtccccagga | gggacagtca | ttctcacttg | tggctccagc | 720 |
| actggagctg | tcaccagcgg | tcattatgcc | aactggttcc | agcagaagcc | tggccaagcc | 780 |
| cccagggcac | ttatatttga | aaccgacaag | aaatattcct | ggacccctgg | ccgattctca | 840 |
| ggctccctcc | ttggggccaa | ggctgccctg | accatctcgg | atgcgcagcc | tgaagatgag | 900 |
| gctgagtatt | actgttcgct | ctccgacgta | gacggttatc | tgttcggagg | aggcacccag | 960 |
| ctgaccgtcc | tatccggaat | tggccgcagg | gccgggatc | cgcggctgca | ggtcgacgaa | 1020 |
| caaaaactca | tctcagaaga | ggatctgaat | gctgtgggcc | aggacacgca | ggaggtcatc | 1080 |
| gtggtgccac | actccttgcc | ctttaaggtg | gtggtgatct | cagccatcct | ggccctggtg | 1140 |
| gtgctcacca | tcatctccct | tatcatcctc | atcatgcttt | ggcagaagaa | gccacgtcca | 1200 |
| cagccggcca | gcaagggcga | ggagctgttc | accggggtgg | tgcccatcct | ggtcgagctg | 1260 |
| gacggcgacg | taaacggcca | caagttcagc | gtgtccggcg | agggcgaggg | cgatgccacc | 1320 |
| tacggcaagc | tgaccctgaa | gctgatctgc | accaccggca | agctgcccgt | gccctggccc | 1380 |
| accctcgtga | ccaccctggg | ctacggcctg | cagtgcttcg | cccgctaccc | cgaccacatg | 1440 |
| aagcagcacg | acttcttcaa | gtccgccatg | cccgaaggct | acgtccagga | gcgcaccatc | 1500 |
| ttcttcaagg | acgacggcaa | ctacaagacc | cgcgccgagg | tgaagttcga | gggcgacacc | 1560 |
| ctggtgaacc | gcatcgagct | gaagggcatc | gacttcaagg | aggacggcaa | catcctgggg | 1620 |
| cacaagctgg | agtacaacta | caacagccac | aacgtctata | tcaccgccga | caagcagaag | 1680 |
| aacggcatca | aggccaactt | caagatccgc | cacaacatcg | aggacggcgg | cgtgcagctc | 1740 |
| gccgaccact | accagcagaa | cacccccatc | ggcgacggcc | ccgtgctgct | gcccgacaac | 1800 |
| cactacctga | gctaccagtc | cgccctgagc | aaagacccca | acgagaagcg | cgatcacatg | 1860 |
| gtcctgctgg | agttcgtgac | cgccgccggg | atcactctcg | gcatggacga | gctgtacaag | 1920 |
| taa | | | | | | 1923 |

<210> SEQ ID NO 2
<211> LENGTH: 10

<212> TYPE: PRT
<213> ORGANISM: Homo sapiens

<400> SEQUENCE: 2

Arg Glu Asp Arg Val Thr Gly Ser Tyr Gln
1               5                   10

<210> SEQ ID NO 3
<211> LENGTH: 11
<212> TYPE: PRT
<213> ORGANISM: Homo sapiens

<400> SEQUENCE: 3

Arg Glu Asp Arg Val Ala Gly Ser Tyr Gln Gly
1               5                   10

<210> SEQ ID NO 4
<211> LENGTH: 640
<212> TYPE: PRT
<213> ORGANISM: Homo sapiens

<400> SEQUENCE: 4

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
                20                  25                  30

Gln Pro Ala Tyr Pro Tyr Asp Val Pro Asp Tyr Ala Leu Gln Ala Ser
                35                  40                  45

Gly Gly Gly Gly Ser Gly Gly Gly Ser Ala Ser Gln Val Gln Leu
50                  55                  60

Val Glu Ser Glu Gly Gly Leu Val Gln Pro Gly Gly Ser Leu Arg Leu
65              70                  75                  80

Ser Cys Ala Ala Ser Gly Phe Thr Phe Ser Ser Tyr Glu Met Asn Trp
                85                  90                  95

Val Arg Gln Ala Pro Gly Lys Gly Leu Glu Trp Val Ser Arg Ile Asp
                100                 105                 110

Gly Asp Gly Ser Ser Thr Asn Tyr Ala Asp Ser Val Lys Gly Arg Phe
                115                 120                 125

Thr Ile Ser Arg Asp Asn Ala Lys Ser Thr Leu Tyr Leu Gln Met Asn
                130                 135                 140

Ser Leu Arg Ala Glu Asp Thr Ala Val Tyr Tyr Cys Thr Arg Ala Arg
145             150                 155                 160

Tyr Phe Gly Ser Val Ser Pro Tyr Gly Met Asp Val Trp Gly Gln Gly
                165                 170                 175

Thr Thr Val Thr Val Ser Ser Gly Ile Leu Gly Ser Asn Ser Arg Glu
                180                 185                 190

Asp Arg Val Thr Gly Ser Tyr Gln Gly Gly Gly Ser Gly Gly Gly
                195                 200                 205

Gly Ser Gly Gly Gly Ser Gln Ala Val Val Thr Gln Glu Pro Ser
        210                 215                 220

Val Thr Val Ser Pro Gly Gly Thr Val Ile Leu Thr Cys Gly Ser Ser
225             230                 235                 240

Thr Gly Ala Val Thr Ser Gly His Tyr Ala Asn Trp Phe Gln Gln Lys
                245                 250                 255

Pro Gly Gln Ala Pro Arg Ala Leu Ile Phe Glu Thr Asp Lys Lys Tyr
                260                 265                 270

Ser Trp Thr Pro Gly Arg Phe Ser Gly Ser Leu Leu Gly Ala Lys Ala

```
                  275                 280                 285
    Ala Leu Thr Ile Ser Asp Ala Gln Pro Glu Asp Glu Ala Glu Tyr Tyr
        290                 295                 300

Cys Ser Leu Ser Asp Val Asp Gly Tyr Leu Phe Gly Gly Gly Thr Gln
    305                 310                 315                 320

Leu Thr Val Leu Ser Gly Ile Gly Arg Arg Gly Arg Asp Pro Arg Leu
                    325                 330                 335

Gln Val Asp Glu Gln Lys Leu Ile Ser Glu Glu Asp Leu Asn Ala Val
                340                 345                 350

Gly Gln Asp Thr Gln Glu Val Ile Val Val Pro His Ser Leu Pro Phe
                355                 360                 365

Lys Val Val Ile Ser Ala Ile Leu Ala Leu Val Val Leu Thr Ile
                370                 375                 380

Ile Ser Leu Ile Ile Leu Ile Met Leu Trp Gln Lys Lys Pro Arg Pro
    385                 390                 395                 400

Gln Pro Ala Ser Lys Gly Glu Glu Leu Phe Thr Gly Val Val Pro Ile
                    405                 410                 415

Leu Val Glu Leu Asp Gly Asp Val Asn Gly His Lys Phe Ser Val Ser
                420                 425                 430

Gly Glu Gly Glu Gly Asp Ala Thr Tyr Gly Lys Leu Thr Leu Lys Leu
                435                 440                 445

Ile Cys Thr Thr Gly Lys Leu Pro Val Pro Trp Pro Thr Leu Val Thr
        450                 455                 460

Thr Leu Gly Tyr Gly Leu Gln Cys Phe Ala Arg Tyr Pro Asp His Met
    465                 470                 475                 480

Lys Gln His Asp Phe Phe Lys Ser Ala Met Pro Glu Gly Tyr Val Gln
                    485                 490                 495

Glu Arg Thr Ile Phe Phe Lys Asp Asp Gly Asn Tyr Lys Thr Arg Ala
                500                 505                 510

Glu Val Lys Phe Glu Gly Asp Thr Leu Val Asn Arg Ile Glu Leu Lys
                515                 520                 525

Gly Ile Asp Phe Lys Glu Asp Gly Asn Ile Leu Gly His Lys Leu Glu
        530                 535                 540

Tyr Asn Tyr Asn Ser His Asn Val Tyr Ile Thr Ala Asp Lys Gln Lys
    545                 550                 555                 560

Asn Gly Ile Lys Ala Asn Phe Lys Ile Arg His Asn Ile Glu Asp Gly
                    565                 570                 575

Gly Val Gln Leu Ala Asp His Tyr Gln Gln Asn Thr Pro Ile Gly Asp
                580                 585                 590

Gly Pro Val Leu Leu Pro Asp Asn His Tyr Leu Ser Tyr Gln Ser Ala
                595                 600                 605

Leu Ser Lys Asp Pro Asn Glu Lys Arg Asp His Met Val Leu Leu Glu
        610                 615                 620

Phe Val Thr Ala Ala Gly Ile Thr Leu Gly Met Asp Glu Leu Tyr Lys
    625                 630                 635                 640

<210> SEQ ID NO 5
<211> LENGTH: 110
<212> TYPE: PRT
<213> ORGANISM: Homo sapiens

<400> SEQUENCE: 5

Gln Ala Val Val Thr Gln Glu Pro Ser Val Thr Val Ser Pro Gly Gly
    1               5                   10                  15
```

Thr Val Ile Leu Thr Cys Gly Ser Ser Thr Gly Ala Val Thr Ser Gly
            20                  25                  30

His Tyr Ala Asn Trp Phe Gln Gln Lys Pro Gly Gln Ala Pro Arg Ala
            35                  40                  45

Leu Ile Phe Glu Thr Asp Lys Lys Tyr Pro Trp Thr Pro Gly Arg Phe
        50                  55                  60

Ser Gly Ser Leu Leu Gly Val Lys Ala Ala Leu Thr Ile Ser Asp Ala
65                  70                  75                  80

Gln Pro Glu Asp Glu Ala Glu Tyr Tyr Cys Leu Leu Ser Asp Val Asp
                85                  90                  95

Gly Tyr Leu Phe Gly Gly Gly Thr Gln Leu Thr Val Leu Ser
            100                 105                 110

<210> SEQ ID NO 6
<211> LENGTH: 110
<212> TYPE: PRT
<213> ORGANISM: Homo sapiens

<400> SEQUENCE: 6

Gln Ala Val Val Thr Gln Glu Pro Ser Val Thr Val Ser Pro Gly Gly
1               5                   10                  15

Thr Val Ile Leu Thr Cys Gly Ser Ser Thr Gly Ala Val Thr Ser Gly
            20                  25                  30

His Tyr Ala Asn Trp Phe Gln Gln Lys Pro Gly Gln Ala Pro Arg Ala
            35                  40                  45

Leu Ile Phe Asp Thr Asp Lys Lys Tyr Pro Trp Thr Pro Gly Arg Phe
        50                  55                  60

Ser Gly Ser Leu Leu Gly Val Lys Ala Ala Leu Thr Ile Ser Asp Ala
65                  70                  75                  80

Gln Pro Glu Asp Glu Ala Glu Tyr Tyr Cys Leu Leu Ser Asp Val Asp
                85                  90                  95

Gly Tyr Leu Phe Gly Gly Gly Thr Gln Leu Thr Val Leu Ser
            100                 105                 110

<210> SEQ ID NO 7
<211> LENGTH: 110
<212> TYPE: PRT
<213> ORGANISM: Homo sapiens

<400> SEQUENCE: 7

Gln Ala Val Val Thr Gln Glu Pro Ser Val Thr Val Ser Pro Gly Gly
1               5                   10                  15

Thr Val Ile Leu Thr Cys Gly Ser Ser Thr Gly Ala Val Thr Ser Gly
            20                  25                  30

His Tyr Ala Asn Trp Phe Gln Gln Lys Pro Gly Gln Ala Pro Arg Ala
            35                  40                  45

Leu Ile Phe Glu Thr Asp Lys Lys Tyr Pro Trp Thr Pro Gly Arg Phe
        50                  55                  60

Ser Gly Ser Leu Leu Gly Val Lys Ala Ala Leu Thr Ile Ser Asp Ala
65                  70                  75                  80

Gln Pro Glu Asp Glu Ala Glu Tyr Tyr Cys Ser Leu Ser Asp Val Asp
                85                  90                  95

Gly Tyr Leu Phe Gly Gly Gly Thr Gln Leu Thr Val Leu Ser
            100                 105                 110

<210> SEQ ID NO 8
<211> LENGTH: 110

<212> TYPE: PRT
<213> ORGANISM: Homo sapiens

<400> SEQUENCE: 8

```
Gln Ala Val Val Thr Gln Glu Pro Ser Val Thr Val Ser Pro Gly Gly
1               5                   10                  15

Thr Val Ile Leu Thr Cys Gly Ser Gly Thr Gly Ala Val Thr Ser Gly
            20                  25                  30

His Tyr Ala Asn Trp Phe Gln Gln Lys Pro Gly Gln Ala Pro Arg Ala
        35                  40                  45

Leu Ile Phe Asp Thr Asp Lys Lys Tyr Pro Trp Thr Pro Gly Arg Phe
    50                  55                  60

Ser Gly Ser Leu Leu Gly Val Lys Ala Ala Leu Thr Ile Ser Asp Ala
65                  70                  75                  80

Gln Pro Glu Asp Glu Ala Glu Tyr Tyr Cys Ser Leu Ser Asp Val Asp
                85                  90                  95

Gly Tyr Leu Phe Gly Gly Gly Thr Gln Leu Thr Val Leu Ser
            100                 105                 110
```

<210> SEQ ID NO 9
<211> LENGTH: 251
<212> TYPE: PRT
<213> ORGANISM: Homo sapiens

<400> SEQUENCE: 9

```
Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Arg Ile Asp Gly Asp Gly Ser Ser Thr Asn Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Arg Tyr Phe Gly Ser Val Ser Pro Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Ser Gly Gly Gly Gly Ser Asp
    130                 135                 140

Ile Arg Val Thr Gln Ser Pro Ser Ser Val Ser Ala Ser Val Gly Asp
145                 150                 155                 160

Arg Val Thr Ile Ser Cys Arg Ala Ser Gln Gly Ile Ala Thr Trp Leu
                165                 170                 175

Gly Trp Tyr Gln Gln Lys Pro Gly Lys Pro Pro Gln Leu Leu Ile Tyr
            180                 185                 190

Ser Ala Ser Thr Leu Gln Thr Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Val Ala Thr Tyr Tyr Cys Gln Glu Gly Ser Thr Phe Pro Leu Thr
225                 230                 235                 240
```

```
Phe Gly Gly Gly Thr Lys Val Asp Ile Lys Ser
                245                 250
```

<210> SEQ ID NO 10
<211> LENGTH: 130
<212> TYPE: PRT
<213> ORGANISM: Homo sapiens

<400> SEQUENCE: 10

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
    50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
        115                 120                 125

Val Ser
    130
```

<210> SEQ ID NO 11
<211> LENGTH: 109
<212> TYPE: PRT
<213> ORGANISM: Homo sapiens

<400> SEQUENCE: 11

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
        35                  40                  45

Lys Asp Thr Glu Arg Pro Ser Gly Ile Pro Glu Arg Phe Ser Gly Thr
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ser Tyr
                85                  90                  95

Val Phe Phe Gly Gly Gly Thr Lys Val Thr Val Leu Ser
            100                 105
```

<210> SEQ ID NO 12
<211> LENGTH: 5
<212> TYPE: PRT
<213> ORGANISM: Homo sapiens

<400> SEQUENCE: 12

```
Gly Gly Gly Gly Ser
1               5
```

-continued

```
<210> SEQ ID NO 13
<211> LENGTH: 10
<212> TYPE: PRT
<213> ORGANISM: Artificial Sequence
<220> FEATURE:
<223> OTHER INFORMATION: GS linker

<400> SEQUENCE: 13

Gly Gly Gly Gly Ser Gly Gly Gly Gly Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: GS linker

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: T2 WT Linker Sequence

<400> SEQUENCE: 15

Lys Pro Arg Ala Pro Arg Gly Thr Pro Phe
1               5                   10

<210> SEQ ID NO 16
<211> LENGTH: 10
<212> TYPE: PRT
<213> ORGANISM: Artificial Sequence
<220> FEATURE:
<223> OTHER INFORMATION: T2 Delta Glycan Linker Sequence

<400> SEQUENCE: 16

Lys Pro Arg Ala Pro Arg Gly Gly Pro Phe
1               5                   10

<210> SEQ ID NO 17
<211> LENGTH: 18
<212> TYPE: PRT
<213> ORGANISM: Artificial Sequence
<220> FEATURE:
<223> OTHER INFORMATION: T3 WT Linker Sequence

<400> SEQUENCE: 17

His Phe Asn Thr Pro Ile Pro Arg Arg His Thr Arg Ser Ala Glu Asp
1               5                   10                  15

Asp Gly

<210> SEQ ID NO 18
<211> LENGTH: 18
<212> TYPE: PRT
<213> ORGANISM: Artificial Sequence
```

-continued

```
<220> FEATURE:
<223> OTHER INFORMATION: T3 Delta Glycan Linker Sequence

<400> SEQUENCE: 18

His Phe Asn Thr Pro Ile Pro Arg Arg His Gly Arg Ser Ala Glu Asp
1               5                   10                  15

Asp Gly
```